United States Patent
Huertas Fernandez et al.

(10) Patent No.: US 11,975,196 B2
(45) Date of Patent: May 7, 2024

(54) TOOLS TO ASSIST SPINAL CORD STIMULATION SELF-REPROGRAMMING

(71) Applicant: Boston Scientific Neuromodulation Corporation, Valencia, CA (US)

(72) Inventors: Ismael Huertas Fernandez, Madrid (ES); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 247 days.

(21) Appl. No.: 16/741,242

(22) Filed: Jan. 13, 2020

(65) Prior Publication Data

US 2020/0147388 A1 May 14, 2020

Related U.S. Application Data

(63) Continuation-in-part of application No. 16/738,786, filed on Jan. 9, 2020, which is a continuation-in-part
(Continued)

(51) Int. Cl.
*A61N 1/36* (2006.01)
*A61N 1/372* (2006.01)
*G16H 40/67* (2018.01)

(52) U.S. Cl.
CPC ..... *A61N 1/36071* (2013.01); *A61N 1/36171* (2013.01); *A61N 1/36175* (2013.01); *A61N 1/37247* (2013.01); *G16H 40/67* (2018.01)

(58) Field of Classification Search
CPC ............ A61N 1/36071; A61N 1/36171; A61N 1/36175; A61N 1/37247; A61N 1/36164;
(Continued)

(56) References Cited

U.S. PATENT DOCUMENTS 6,181,969 B1   1/2001   Gord
6,516,227 B1   2/2003   Meadows et al.
(Continued)

FOREIGN PATENT DOCUMENTS

CN   202933390      5/2013
EP   2923727        9/2015
WO   2017/106539    6/2017

OTHER PUBLICATIONS

International Search Report and Written Opinion regarding corresponding PCT Application No. PCT/US2020/013344, dated Apr. 9, 2020.
(Continued)

*Primary Examiner* — Joseph M Dietrich
*Assistant Examiner* — Ranjani Mari Sundaresan
(74) *Attorney, Agent, or Firm* — Lewis & Reese, PLLC

(57) ABSTRACT

Methods and systems for assisting a patient to reprogram parameters of an implantable medical device, such as a spinal cord stimulator, are disclosed. A patient may use an external controller, which may be either a dedicated device or a personal computing device, to interact with their implantable medical device and evaluate the efficacy of their therapy. If the efficacy diminishes, the patient may use their external controller to adjust either the neural dosage (i.e., frequency, pulse width, and/or amplitude) and/or the location at which stimulation is provided. A reprogramming assistant is provided, which guides the patient in adjusting their stimulation using their external controller. The patient may use supra-perception or sub-perception stimulation for the adjustment. The implantable medical device may include pre-programmed "rescue programs" to assist the patient in recovering the efficacy of their therapy.

17 Claims, 17 Drawing Sheets

Related U.S. Application Data of application No. 16/657,560, filed on Oct. 18, 2019, which is a continuation-in-part of application No. 16/460,640, filed on Jul. 2, 2019, and a continuation-in-part of application No. 16/460,655, filed on Jul. 2, 2019, now Pat. No. 11,338,127, which is a continuation-in-part of application No. 16/100,904, filed on Aug. 10, 2018, now Pat. No. 10,576,282.

(60) Provisional application No. 62/803,330, filed on Feb. 8, 2019, provisional application No. 62/803,200, filed on Feb. 8, 2019, provisional application No. 62/693,543, filed on Jul. 3, 2018, provisional application No. 62/544,656, filed on Aug. 11, 2017.

(58) Field of Classification Search
CPC ............. A61N 1/3615; A61N 1/36062; A61N 1/36146; G16H 40/67; G16H 20/40
See application file for complete search history.

(56) References Cited

U.S. PATENT DOCUMENTS

| | | | |
|---|---|---|---|
| 7,463,927 B1 | 12/2008 | Chaouat | |
| 7,603,177 B2 | 10/2009 | Sieracki et al. | |
| 8,180,451 B2 | 5/2012 | Hickman et al. | |
| 8,359,102 B2 | 1/2013 | Alataris et al. | |
| 8,515,546 B2 | 8/2013 | Goddard et al. | |
| 8,606,362 B2 | 12/2013 | He et al. | |
| 8,620,436 B2 | 12/2013 | Parramon et al. | |
| 8,712,533 B2 | 4/2014 | Alataris et al. | |
| 8,792,988 B2 | 7/2014 | Alataris et al. | |
| 9,259,574 B2 | 2/2016 | Aghassian et al. | |
| 9,327,125 B2 | 5/2016 | Alataris et al. | |
| 9,333,357 B2 | 5/2016 | Alataris et al. | |
| 9,446,243 B2 | 9/2016 | Marnfeldt et al. | |
| 9,480,842 B2 | 11/2016 | Alataris et al. | |
| 9,789,252 B2 | 10/2017 | Gerber et al. | |
| 2010/0023090 A1 | 1/2010 | Jaax et al. | |
| 2010/0274312 A1 | 10/2010 | Alataris et al. | |
| 2012/0092031 A1 | 4/2012 | Shi et al. | |
| 2012/0095519 A1 | 4/2012 | Parramon et al. | |
| 2012/0095529 A1 | 4/2012 | Parramon et al. | |
| 2013/0053923 A1 | 2/2013 | Jaax et al. | |
| 2013/0268026 A1 | 10/2013 | Rao et al. | |
| 2014/0277251 A1 | 9/2014 | Gerber et al. | |
| 2014/0364919 A1 | 12/2014 | Doan | |
| 2015/0080982 A1 | 3/2015 | Funderburk | |
| 2015/0231402 A1 | 8/2015 | Aghassian | |
| 2015/0335893 A1 | 11/2015 | Parker | |
| 2015/0360038 A1 | 12/2015 | Zottola et al. | |
| 2016/0082265 A1 | 3/2016 | Moffitt et al. | |
| 2016/0114166 A1 | 4/2016 | Kaula et al. | |
| 2016/0144183 A1 | 5/2016 | Marnfeldt | |
| 2016/0158551 A1 | 6/2016 | Kent et al. | |
| 2016/0228706 A1* | 8/2016 | Hershey | A61N 1/37247 |
| 2016/0317815 A1* | 11/2016 | Doan | A61N 1/0551 |
| 2016/0361543 A1 | 12/2016 | Kaula et al. | |
| 2016/0367822 A1 | 12/2016 | Parramon | |
| 2017/0050035 A1* | 2/2017 | Gupta | A61N 1/36021 |
| 2017/0056642 A1 | 3/2017 | Moffitt et al. | |
| 2017/0106197 A1 | 4/2017 | Wechter et al. | |
| 2017/0165490 A1 | 6/2017 | Wechter | |
| 2017/0173335 A1 | 6/2017 | Min et al. | |
| 2017/0189685 A1 | 7/2017 | Steinke et al. | |
| 2017/0348530 A1 | 12/2017 | Doan et al. | |
| 2017/0348540 A1 | 12/2017 | Doan et al. | |
| 2018/0043172 A1 | 2/2018 | Serrano Carmona | |
| 2018/0071513 A1 | 3/2018 | Weiss et al. | |
| 2018/0071520 A1 | 3/2018 | Weerakoon et al. | |
| 2018/0104493 A1 | 4/2018 | Doan et al. | |
| 2019/0046800 A1 | 2/2019 | Doan et al. | |
| 2019/0083796 A1 | 3/2019 | Weerakoon et al. | |
| 2019/0175915 A1 | 6/2019 | Brill et al. | |
| 2019/0209844 A1 | 7/2019 | Esteller et al. | |
| 2019/0290900 A1 | 9/2019 | Esteller et al. | |
| 2019/0344083 A1 | 11/2019 | Marnfeldt et al. | |
| 2019/0366094 A1 | 12/2019 | Esteller et al. | |
| 2019/0366104 A1 | 12/2019 | Doan et al. | |
| 2020/0009367 A1 | 1/2020 | Huertas Fernandez et al. | |
| 2020/0009394 A1 | 1/2020 | Huertas Fernandez et al. | |

OTHER PUBLICATIONS

U.S. Appl. No. 62/825,982, Wagenbach et al., filed Mar. 29, 2019.
U.S. Appl. No. 62/849,642, Zhang et al., filed May 17, 2019.
U.S. Appl. No. 62/860,627, Esteller et al., filed Jun. 12, 2019.
U.S. Appl. No. 16/657,560, Moffitt et al., filed Oct. 18, 2019.
U.S. Appl. No. 16/661,549, Esteller et al., filed Oct. 23, 2019.
L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
S. Thomson et al., "The PROCO Randomised Controlled Trial: Effects of Pulse Rate on Clinical Outcomes in Kilohertz Frequency Spinal Cord Stimulation—A Multicentre, Double-blind, Crossover Study," presented at the International Neuromodulation Society (INS) Meeting on May 31, 2017.
E.C. Celik et al., "The effect of low-frequency TENS in the treatment of neuropathic pain in patients with spinal cord injury," Spinal Cord 51:34-337 (2013).
Y. Maeda et al., "Low frequencies, but not high frequencies of bi-polar spinal cord stimulation reduce cutaneous and muscle hyperalgesia induced by nerve injury," Pain 138:143-152 (2008).
S. Thomson et al., "Neural Dosing and Energy Requirements in Kilohertz Frequency Spinal Cord Stimulation (SCS)," poster presented at the International Neuromodulation Society (INS) Meeting on May 31, 2017.
S. Paz et al., "Improved Efficacy of SCS Implants Using Multiple Waveforms and Field Shape Options," poster presented at the International Neuromodulation Society (INS) Meeting on May 31, 2017.
S. Paz et al., "Evaluation of Customized Field Shape for Subperception SCS in a Case Series of Chronic Pain Patients," poster presented at the North American Neuromodulation Society (NANS) Meeting on Jan. 11-14, 2018.
S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).
J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).
Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.
Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.
Yearwood, Thomas, "Neuropathic Extremity Paid and Spinal Cord Stimulation," Pain Medicine, vol. 7, No. S1, 2006, 6 pages.

* cited by examiner

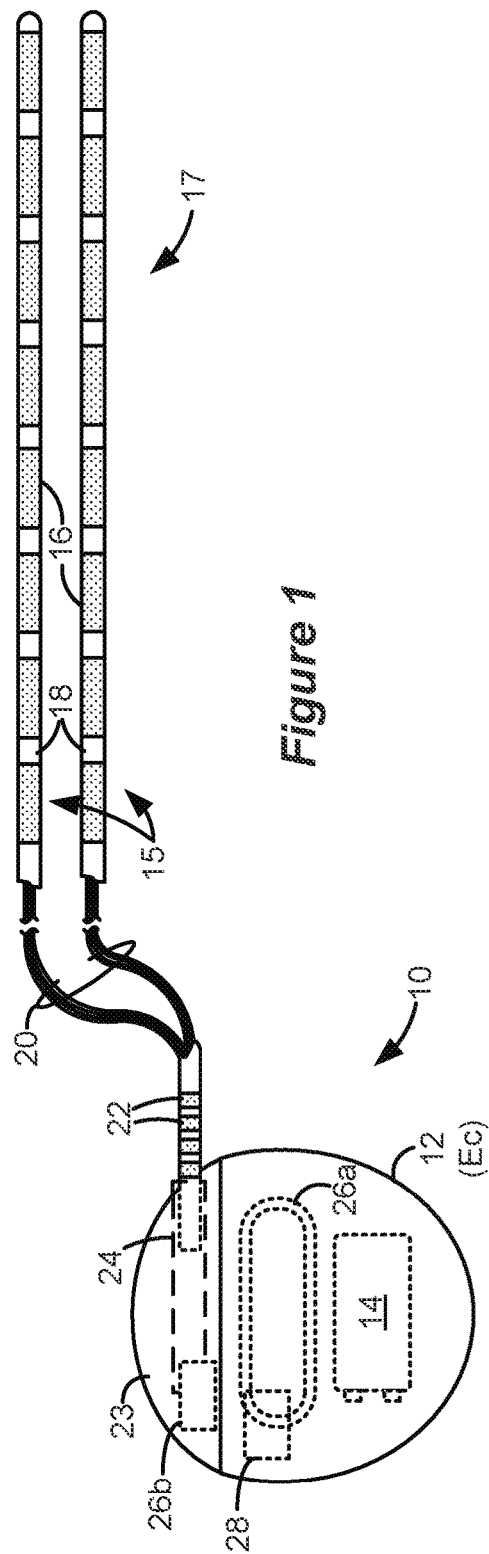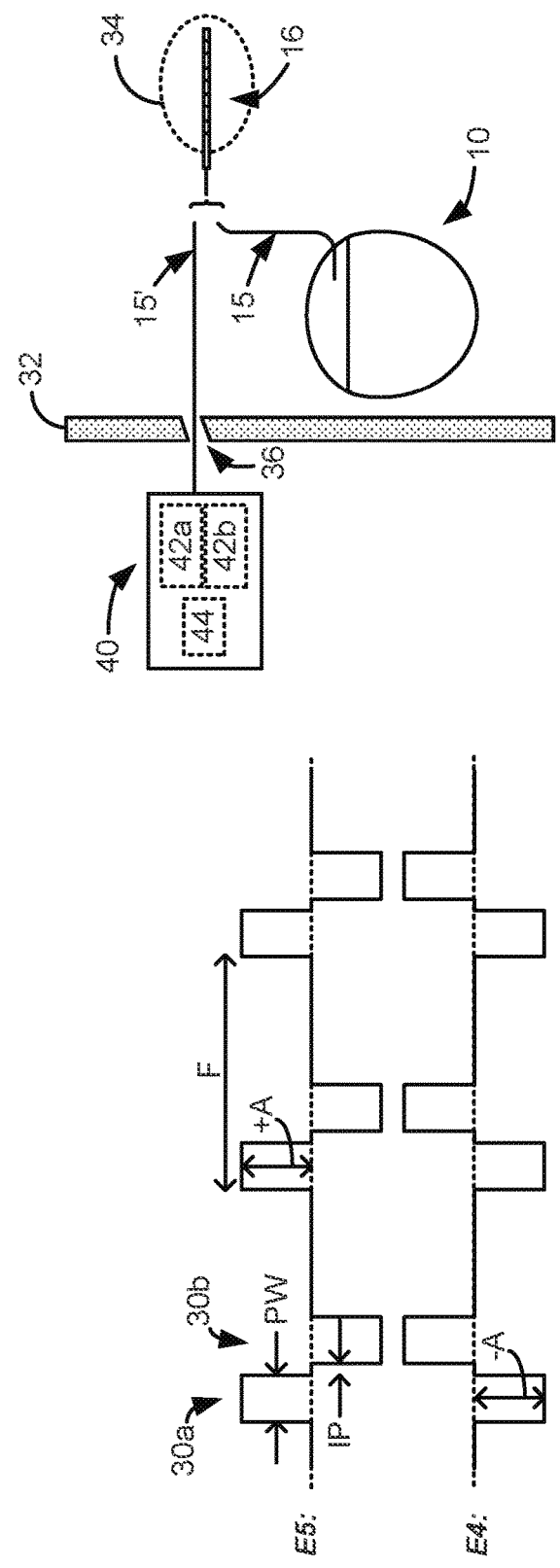

| Reprogramming Assistant (RA) ||
|---|---|
| Evaluation Module (EM) | Reprogramming Module (RPM) |
| • Evaluate and Track Efficacy<br>• Data Gathering<br>• Determine/Adjust Neural Dosage<br>• Determine if Reprogramming is Warranted | • Guide Patient Self-Reprogramming<br>• Stimulation Location Correction<br>• Paresthesia Based and Non-paresthesia Based Pre-Loaded "Rescue Programs"<br>• Adjust Stimulation Parameters/Neural Dosage<br>• Determine if Clinician Visit Necessary |

*Figure 8A*

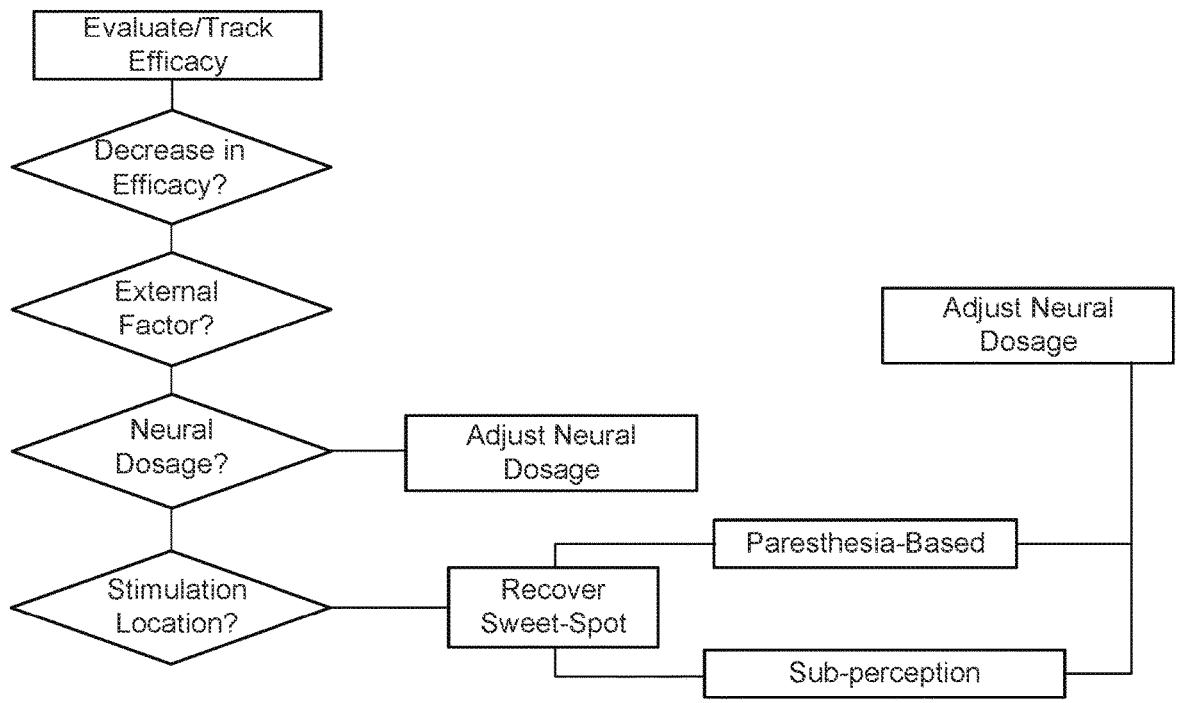

*Figure 8B*

| Reprogramming Assistant ||||
|---|---|---|---|
| Stimulation Location Module || Neural Dosage Module ||
| Paresthesia | Sub-Paresthesia | Paresthesia | Sub-Paresthesia |
| Paresthesia Rescue Locations (PRL)<br><br>• Schedule of Pre-loaded Programs | Anatomical Location Schedule (ALS)<br><br>• Schedule of Pre-loaded Programs | Supra-Perception<br><br>• Low Frequencies | Sub-Perception<br><br>• All Frequencies<br>• Neural Dose Relationships |
| Center Point of Stimulation Adjustment Module (CPSM)<br><br>• Patient-controlled search for new stimulation location. | | | |

*Figure 11*

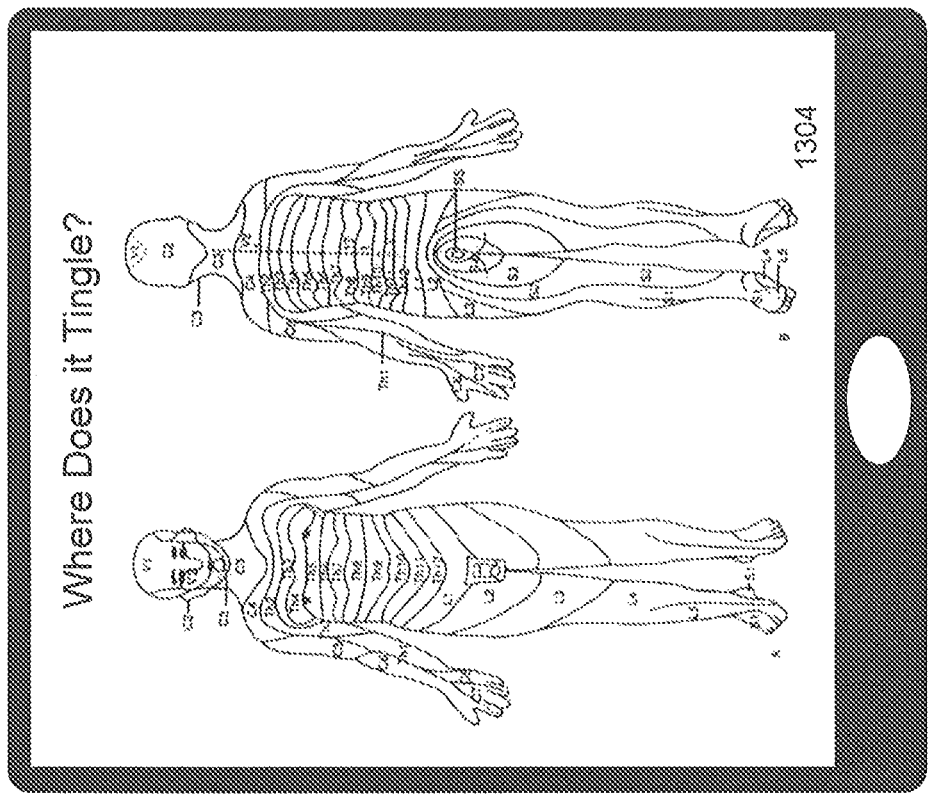
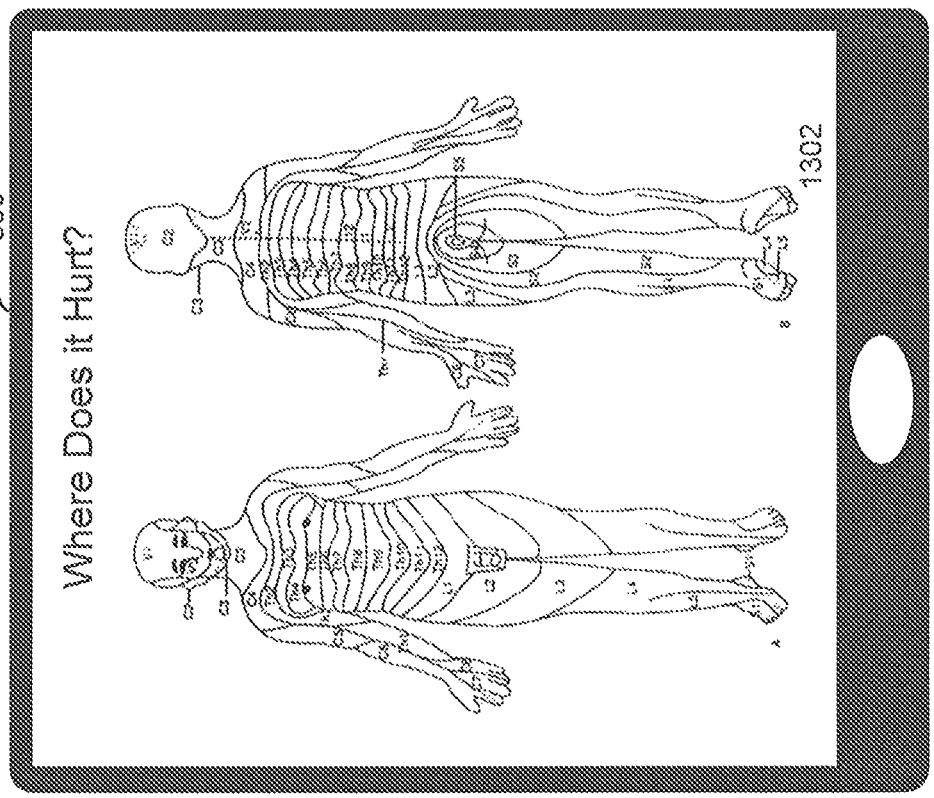
Figure 13

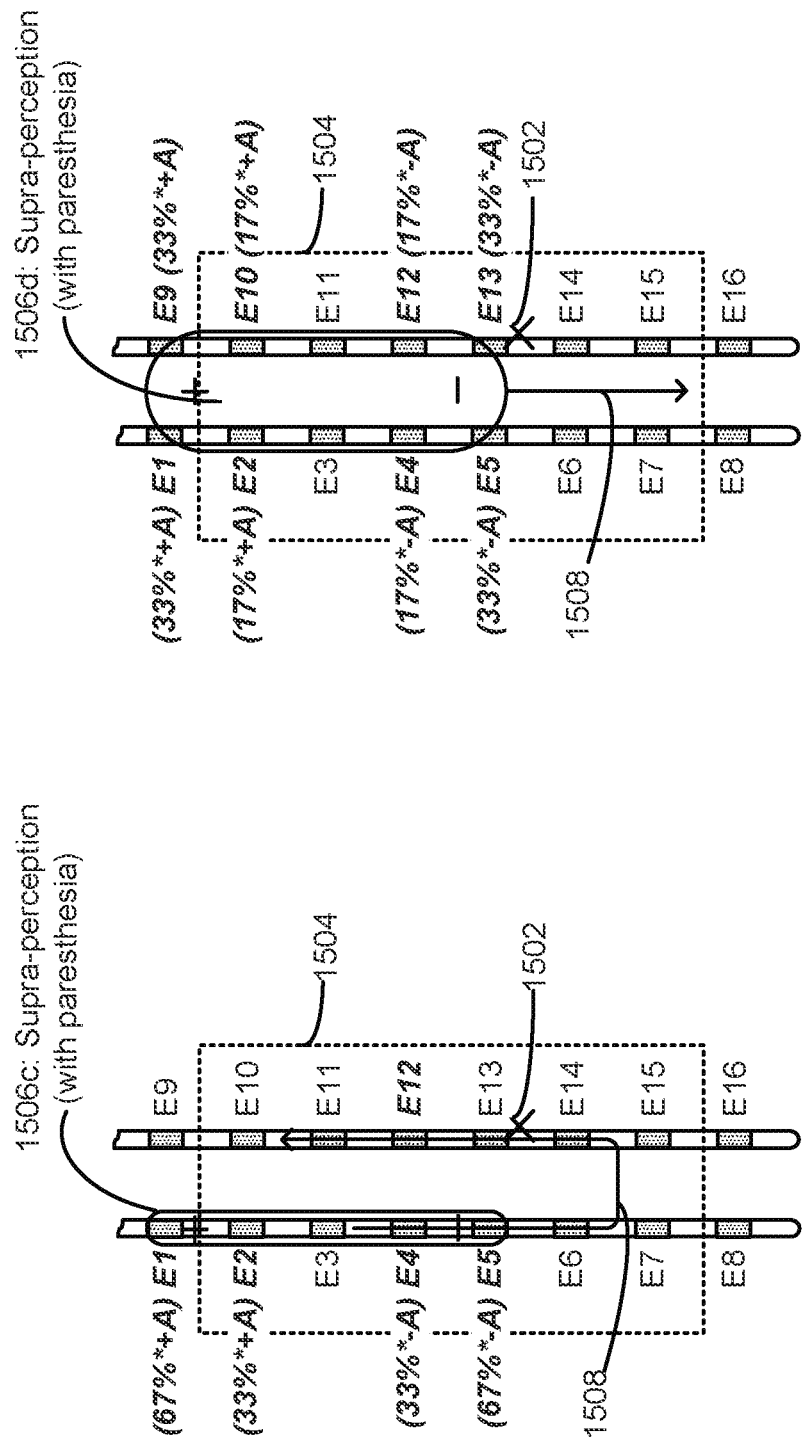

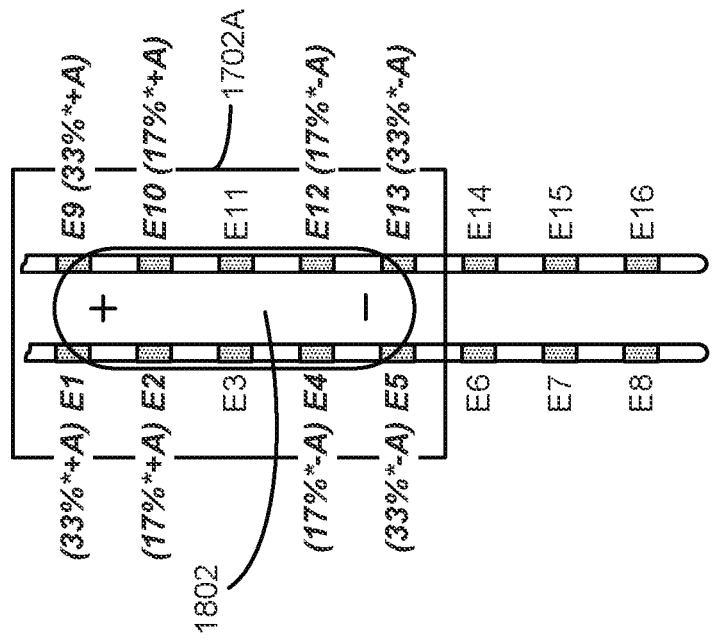

TOOLS TO ASSIST SPINAL CORD STIMULATION SELF-REPROGRAMMING

CROSS REFERENCE TO RELATED APPLICATIONS

This application is a non-provisional application of U.S. Provisional Patent Application Ser. No. 62/803,200, filed Feb. 8, 2019.
This application is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of;
   U.S. patent application Ser. No. 16/100,904, filed Aug. 10, 2018, which is a non-provisional application of U.S. Provisional Patent Application Ser. Nos. 62/693,543, filed Jul. 3, 2018, and 62/544,656, filed Aug. 11, 2017;
   U.S. patent application Ser. No. 16/460,640, filed Jul. 2, 2019, which is a non-provisional application of U.S. Provisional Patent Application Ser. No. 62/803,330, filed Feb. 8, 2019; and
   U.S. patent application Ser. No. 16/460,655, filed Jul. 2, 2019, which is a non-provisional application of U.S. Provisional Patent Application Ser. No. 62/803,330, filed Feb. 8, 2019.
Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of control and programming of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

SUMMARY

Disclosed herein is a method of providing spinal cord stimulation (SCS) therapy to a patient using a spinal cord stimulator comprising an implantable pulse generator (IPG) and a plurality of electrodes implantable in the patient and an external controller for controlling the IPG. According to some embodiments, the method comprises enabling the IPG to provide stimulation to the patient, using a graphical user interface (GUI) on a screen of the external controller to determine an indication of efficacy of the provided stimulation, based on the indication of efficacy, automatically determining via an evaluation algorithm in the external controller, whether to perform a reprogramming algorithm in the external controller to adjust one or more stimulation parameters. According to some embodiments, the reprogramming algorithm: determines whether to use sub-perception stimulation or supra-perception stimulation for reprogramming, if sub-perception stimulation is determined for reprogramming, performs a sub-perception reprogramming algorithm in the external controller to reprogram the IPG, and if supra-perception stimulation is determined for reprogramming, performs a supra-perception reprogramming algorithm in the external controller to reprogram the IPG. According to some embodiments, the external controller is a hand-held mobile computing device. According to some embodiments, determining whether to perform a reprogramming algorithm comprises comparing the determined indication of efficacy to a history of prior indications of efficacy to determine a trend of efficacy indications. According to some embodiments, the indication of efficacy comprises a patient rating of the efficacy. According to some embodiments, determining whether to use sub-perception stimulation or supra-perception stimulation for reprogramming comprises obtaining an indication from the patient indicating a preference for reprogramming using sub-perception stimulation or supra-perception stimulation. According to some embodiments, the sub-perception reprogramming algorithm comprises: enabling the IPG to sequentially perform a plurality of stimulation programs, wherein each stimulation program comprises stimulation parameters that provide sub-perception stimulation to a different anatomical location of the patient, for each stimulation program, determining an indication of efficacy of the stimulation provided at the different anatomical location, based on the indications of efficacy of the stimulation provided at the different anatomical locations, determining a best anatomical location for stimulation, and reprogramming the IPG to provide stimulation to the determined best anatomical location. According to some embodiments, the plurality of stimulation programs is pre-loaded in the IPG. According to some embodiments, the indications of efficacy of the stimulation provided at the different anatomical locations comprise patient ratings of the efficacy of the stimulation provided at the different anatomical locations. According to some embodiments, the sub-perception reprogramming algorithm further comprises adjusting the neural dose of the stimulation provided at the determined best anatomical location. According to some embodiments, the supra-perception reprogramming algorithm comprises: determining whether to use pre-loaded rescue stimulation locations or patient-controlled stimulation locations for reprogramming, if using pre-loaded rescue stimulation locations for reprogramming is determined, performing a rescue location algorithm, and if using patient-controlled stimulation locations for reprogramming is determined, performing a patient-controlled location algorithm. According to some embodiments, the rescue location algorithm comprises: enabling the IPG to sequentially perform a plurality of stimulation programs, wherein each stimulation program comprises stimulation parameters that provide supra-perception stimulation at different locations in the patient, for each stimulation program, determining an indication of the patient's satisfaction with the supra-perception stimulation, based on the indications of the patient's satisfaction, determining a best location for stimulation, and reprogramming the IPG to provide stimulation to the determined best location. According to some embodiments, the plurality of stimulation programs is pre-loaded in the IPG. According to some embodiments, the indication of the patient's satisfaction with the supra-perception stimulation indicates an overlap of paresthesia evoked by the stimulation with the patient's pain. According to some embodiments, the supra-perception reprogramming algorithm further comprises adjusting the neural dose of the stimulation provided at the determined best location. According to some embodiments, the patient-controlled location algorithm comprises: enabling the IPG to provide supra-perception stimulation at a first location, obtaining an indication from the patient indicating the patient's satisfaction with the supra-perception stimulation at the first location, enabling the IPG to move the supra-perception stimulation from a first location to a new location, obtaining an indication from the patient indicating the patient's satisfaction with the supra-perception stimulation at the new location, based on the indications of the patient's satisfaction, determining a best location for stimulation, and reprogramming the IPG to provide stimulation to the determined best location. According to some embodiments, the indication of the patient's satisfaction with the supra-perception stimulation indicates an overlap of paresthesia evoked by the stimulation with the patient's pain. According to some embodiments, the supra-perception reprogramming algorithm further comprises adjusting the neural dose of the stimulation provided at the determined best location.

Also disclosed herein is a method of providing spinal cord stimulation (SCS) therapy to a patient using a spinal cord stimulator comprising an implantable pulse generator (IPG) and a plurality of electrodes implantable in the patient and an external controller for controlling the IPG, the method comprising: enabling the IPG to provide stimulation to the patient, using a graphical user interface (GUI) on a screen of the external controller to determine an indication of efficacy of the provided stimulation, based on the indication of efficacy, automatically determining via an evaluation algorithm in the external controller, whether to perform a reprogramming algorithm in the external controller to adjust one or more stimulation parameters, wherein the reprogramming algorithm: changes stimulation from sub-perception stimulation to supra-perception stimulation, obtains an indication from the patient indicating the patient's satisfaction with the supra-perception stimulation, if the patient is dissatisfied with the supra-perception stimulation, enables the IPG to move the supra-perception stimulation from a first location to a new location, obtains an indication from the patient the patient's satisfaction with the supra-perception stimulation at the new location, and if the is satisfied with the supra-perception stimulation at the new location, changes stimulation from supra-perception stimulation to sub-perception stimulation at the new location.

Also disclosed herein is a non-transitory computer readable medium executable on an external controller configured to communicate with a spinal cord stimulator comprising an implantable pulse generator (IPG) and a plurality of electrodes implantable in a patient, wherein the non-transitory computer readable medium comprises instructions, which when executed by the external controller, configure the external controller. According to some embodiments, the instructions configure the external controller to: use a graphical user interface (GUI) on a screen of the external controller to determine an indication of efficacy of stimulation provided to the patient by the IPG, based on the indication of efficacy, automatically determine via an evaluation algorithm in the external controller, whether to perform a reprogramming algorithm in the external controller to adjust one or more stimulation parameters. According to some embodiments, the reprogramming algorithm: changes stimulation from sub-perception stimulation to supra-perception stimulation, obtains an indication from the patient indicating the patient's satisfaction with the supra-perception stimulation, if the patient is dissatisfied with the supra-perception stimulation, enables the IPG to move the supra-perception stimulation from a first location to a new location, obtains an indication from the patient the patient's satisfaction with the supra-perception stimulation at the new location, and if the is satisfied with the supra-perception stimulation at the new location, changes stimulation from supra-perception stimulation to sub-perception stimulation at the new location.

Also disclosed herein is a non-transitory computer readable medium executable on an external controller configured to communicate with a spinal cord stimulator comprising an implantable pulse generator (IPG) and a plurality of electrodes implantable in a patient, wherein the non-transitory computer readable medium comprises instructions, which when executed by the external controller, configure the external controller to: use a graphical user interface (GUI) on a screen of the external controller to determine an indication of efficacy of stimulation provided to the patient by the IPG, based on the indication of efficacy, automatically determine via an evaluation algorithm in the external controller, whether to perform a reprogramming algorithm in the external controller to adjust one or more stimulation parameters. According to some embodiments, the reprogramming algorithm: determines whether to use sub-perception stimulation or supra-perception stimulation for reprogramming, if sub-perception stimulation is determined for reprogramming, performs a sub-perception reprogramming algorithm in the external controller to reprogram the IPG, and if supra-perception stimulation is determined for reprogramming, performs a supra-perception reprogramming algorithm in the external controller to reprogram the IPG. According to some embodiments, the external controller is a hand-held mobile computing device. According to some embodiments, determining whether to perform a reprogramming algorithm comprises comparing the determined indication of efficacy to a history of prior indications of efficacy to determine a trend of efficacy indications. According to some embodiments, the indication of efficacy comprises a patient rating of the efficacy. According to some embodiments, determining whether to use sub-perception stimulation or supra-perception stimulation for reprogramming comprises obtaining an indication from the patient indicating a preference for reprogramming using sub-perception stimulation or supra-perception stimulation. According to some embodiments, the sub-perception reprogramming algorithm comprises: enabling the IPG to sequentially perform a plurality of stimulation programs, wherein each stimulation program comprises stimulation parameters that provide sub-perception stimulation to a different anatomical location of the patient, for each stimulation program, determining an indication of efficacy of the stimulation provided at the different anatomical location, based on the indications of efficacy of the stimulation provided at the different anatomical locations, determining a best anatomical location for stimulation, and reprogramming the IPG to provide stimulation to the determined best anatomical location. According to some embodiments, the plurality of stimulation programs is pre-loaded in the IPG. According to some embodiments, the indications of efficacy of the stimulation provided at the different anatomical locations comprise patient ratings of the efficacy of the stimulation provided at the different anatomical locations. According to some embodiments, the sub-perception reprogramming algorithm further comprises adjusting the neural dose of the stimulation provided at the determined best anatomical location. According to some embodiments, the supra-perception reprogramming algorithm comprises: determining whether to use pre-loaded rescue stimulation locations or patient-controlled stimulation locations for reprogramming, if using pre-loaded rescue stimulation locations for reprogramming is determined, performing a rescue location algorithm, and if using patient-controlled stimulation locations for reprogramming is determined, performing a patient-controlled location algorithm. According to some embodiments, the rescue location algorithm comprises: enabling the IPG to sequentially perform a plurality of stimulation programs, wherein each stimulation program comprises stimulation parameters that provide supra-perception stimulation at different locations in the patient, for each stimulation program, determining an indication of the patient's satisfaction with the supra-perception stimulation, based on the indications of the patient's satisfaction, determining a best location for stimulation, and reprogramming the IPG to provide stimulation to the determined best location. According to some embodiments, the plurality of stimulation programs is pre-loaded in the IPG. According to some embodiments, the indication of the patient's satisfaction with the supra-perception stimulation indicates an overlap of paresthesia evoked by the stimulation with the patient's pain. According to some embodiments, the supra-perception reprogramming algorithm further comprises adjusting the neural dose of the stimulation provided at the determined best location. According to some embodiments, the patient-controlled location algorithm comprises: enabling the IPG to provide supra-perception stimulation at a first location, obtaining an indication from the patient indicating the patient's satisfaction with the supra-perception stimulation at the first location, enabling the IPG to move the supra-perception stimulation from a first location to a new location, obtaining an indication from the patient indicating the patient's satisfaction with the supra-perception stimulation at the new location, based on the indications of the patient's satisfaction, determining a best location for stimulation, and reprogramming the IPG to provide stimulation to the determined best location. According to some embodiments, the indication of the patient's satisfaction with the supra-perception stimulation indicates an overlap of paresthesia evoked by the stimulation with the patient's pain. According to some embodiments, the supra-perception reprogramming algorithm further comprises adjusting the neural dose of the stimulation provided at the determined best location.

BRIEF DESCRIPTION OF THE DRAWINGS

FIG. 1 shows an Implantable Pulse Generator (IPG) useable for Spinal Cord Stimulation (SCS).

FIG. 2 shows an example of stimulation pulses producible by the IPG.

FIG. 3 shows use of an External Trial Stimulator (ETS) useable to provide stimulation before implantation of an IPG.

FIGS. 8A-8B show aspects of a reprogramming assistant (RA).

FIG. 11 shows aspects of a reprogramming module (RPM).

FIG. 13 shows an implementation of a reprogramming module (RPM).

FIGS. 15A-15D show sweet-spot searching.

FIG. 17 shows an implementation of an anatomical location schedule (ALS).

FIG. 18 shows a large virtual bipole for stimulating an anatomical location.

DETAILED DESCRIPTION

Figure 4:
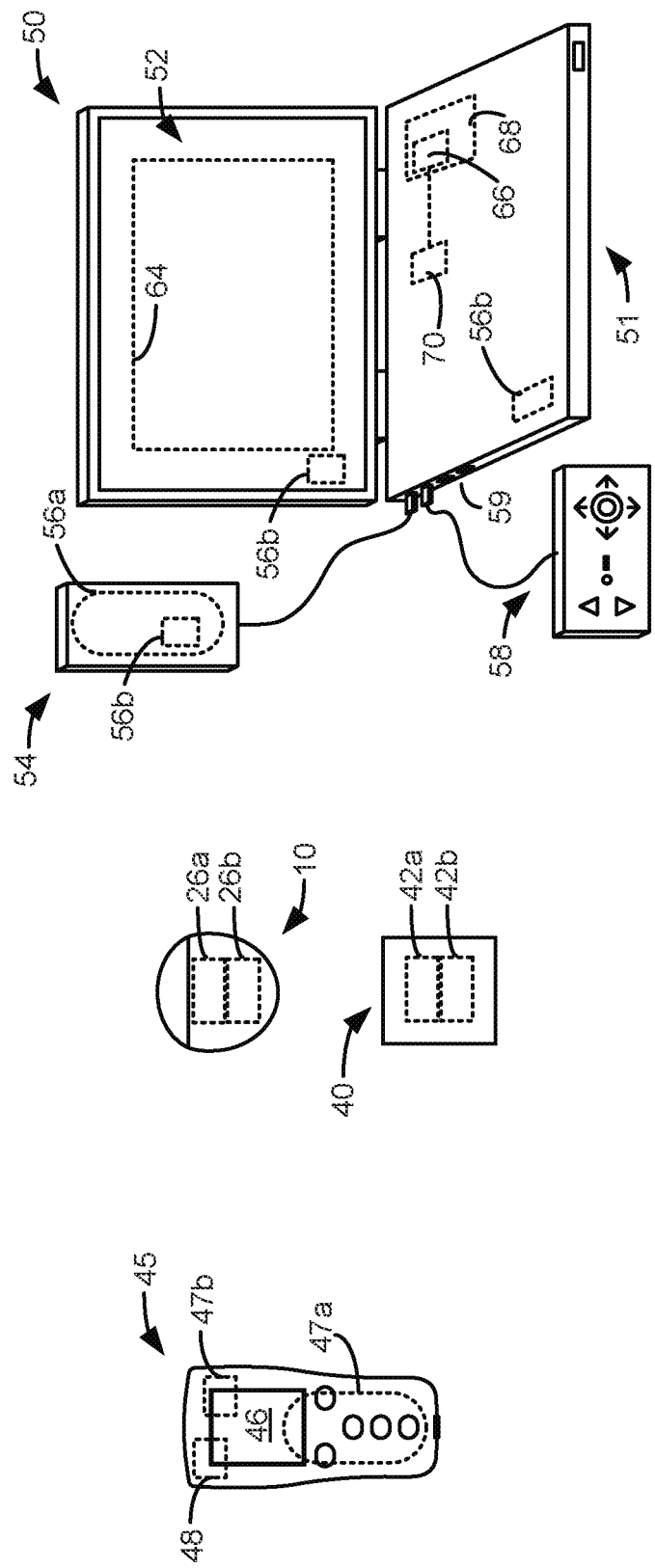
FIG. 4 shows various external devices capable of communicating with and programming stimulation in an IPG and ETS.

An SCS system typically includes an implantable medical device (IMD), specifically an Implantable Pulse Generator (IPG) 10, as shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude+A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Stimulation circuitry 28 can for example comprise the circuitry described in U.S. Pat. Nos. 8,606,362, 8,606,362, 8,620,436, 10,576,265 and 11,040,192. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone or tablet which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters and create a stimulation program to be wirelessly transmitted to the IPG 10 or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 40 can depend on the type of antennas included in those devices. If the patient's IPG 10 or ETS 40 includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

In an SCS application, it is desirable to determine one or more stimulation programs that will be effective for each patient to relieve their symptoms, such as pain. A significant part of determining an effective stimulation program is to determine the electrodes that should be selected to provide the stimulation. The neural site at which pain originates in a patient, and therefore electrodes proximate to such neural site, can be difficult to determine, and experimentation is typically undertaken to select the best combination of electrodes to provide a patient's therapy. In other words, the clinician seeks to determine a combination of electrodes that provides a center point of stimulation (CPS) that best addresses the patient's symptoms.

To program stimulation programs or parameters for the IPG 10 or ETS 40 (sometimes referred to as a "fitting process"), the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

Figure 5:
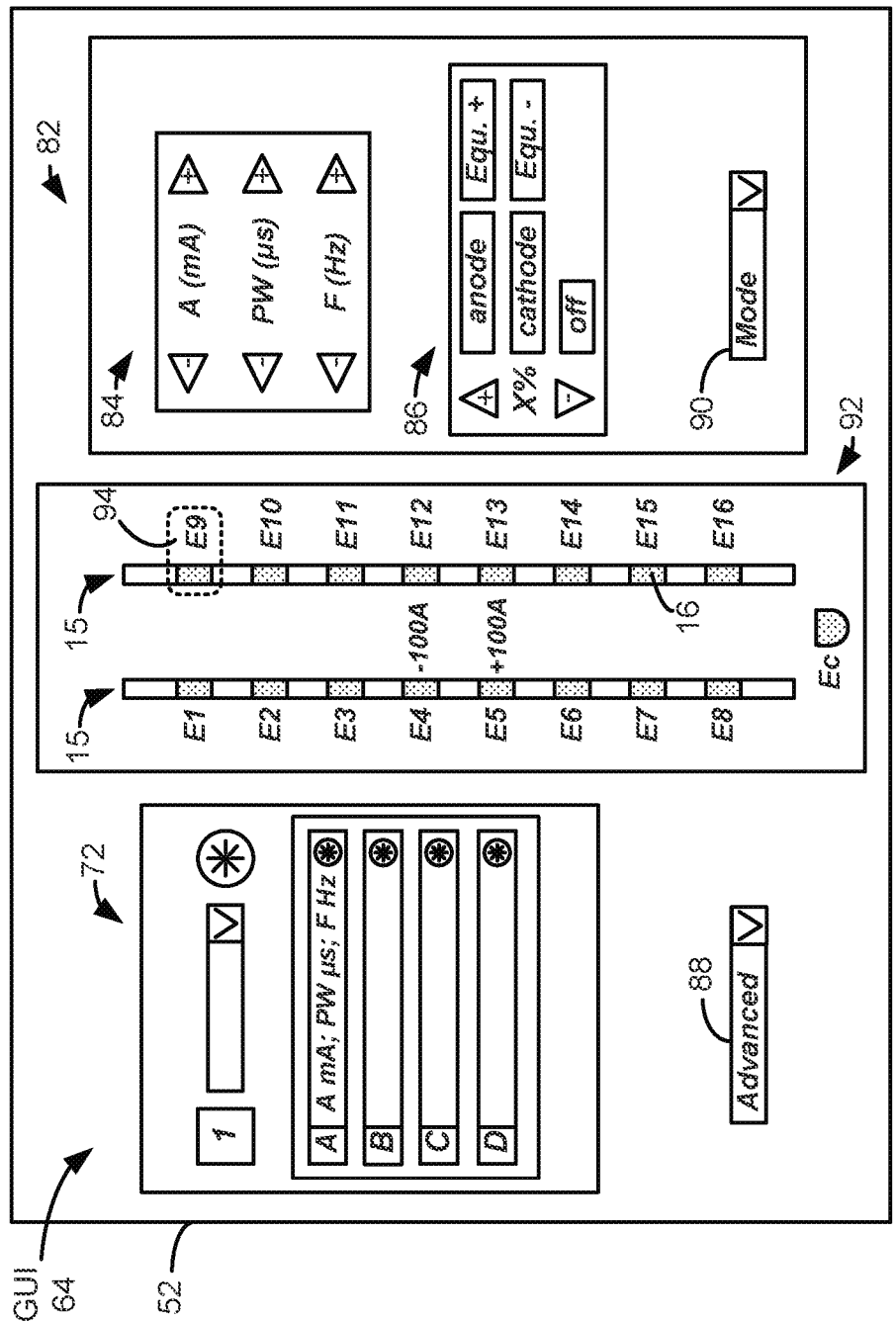
FIG. 5 shows a Graphical User Interface (GUI) of a clinician programmer external device for setting or adjusting stimulation parameters.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

SCS traditionally provides a sensation of paresthesia to a patient—i.e., a sensation such as tingling, prickling, heat, cold, etc. that can accompany SCS therapy. Selecting electrodes for a given patient can be easier when paresthesia is present because the patient can provide feedback to the clinician concerning when the paresthesia seems to "cover" the area that is causing pain. In other words, the patient can generally assess when the sensation of paresthesia has replaced the sensation of pain, which assists in electrode selection.

Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies. Electrode selection for a given patient can be more difficult when paresthesia is not present because the patient does not feel the stimulation and therefore it can be difficult for the patient to feel whether the stimulation is covering his pain. Further, sub-threshold stimulation therapy may require a "wash in" period before it can become effective. A wash in period can take up to a day or more, and therefore sub-threshold stimulation may not be immediately effective, making electrode selection more difficult.

U.S. Pat. Nos. 10,576,282 and 11,160,987, both of which are hereby incorporated herein by reference, relate to programming stimulation parameters for sub-perception therapy. For example, the '282 Patent discloses methods whereby supra-perception stimulation is used during the fitting process to identify electrodes that might provide effective therapy, i.e., to identify a combination of electrodes that provides a CPS at the "sweet spot" for treating the patient. The '282 Patent also discloses particular combinations of stimulation parameters, such as pulse widths and frequencies, which have been discovered to provide good sub-perception therapy while optimizing power consumption.

Once the clinician has determined one or more stimulation programs believed to be effective for treating the patient, those programs may be saved within non-volatile memory within the IPG 10. As explained in more detail below, the patient can use their external controller 45 to select a particular program from the bank of saved programs, depending on the patient's need. For example, some patients may generally prefer sub-perception therapy programs, but they may want at least one supra-perception therapy program for certain occasions.

Once the patient has been released with a programmed IPG, the patient may wish to make adjustments to their therapy. To do so, they may use an external controller. External devices such as the external controller 45 of FIG. 4 were historically built by the manufacturer of the IMDs, and thus were generally dedicated to communicate only with such IMDs. However, there are many commercial mobile devices, such as cell phones, that have user interfaces and built-in communication means suitable for functioning as a wireless external controller for an IMD. Using such portable hand-held mobile devices as external controllers for IMDs benefit both manufacturers and patients: manufacturers would not need to design, build, and test dedicated external controllers, and patients could control and communicate with their IMDs without the inconvenience of having to carry and purchase additional custom external controllers.

Figures 6A, 6B:
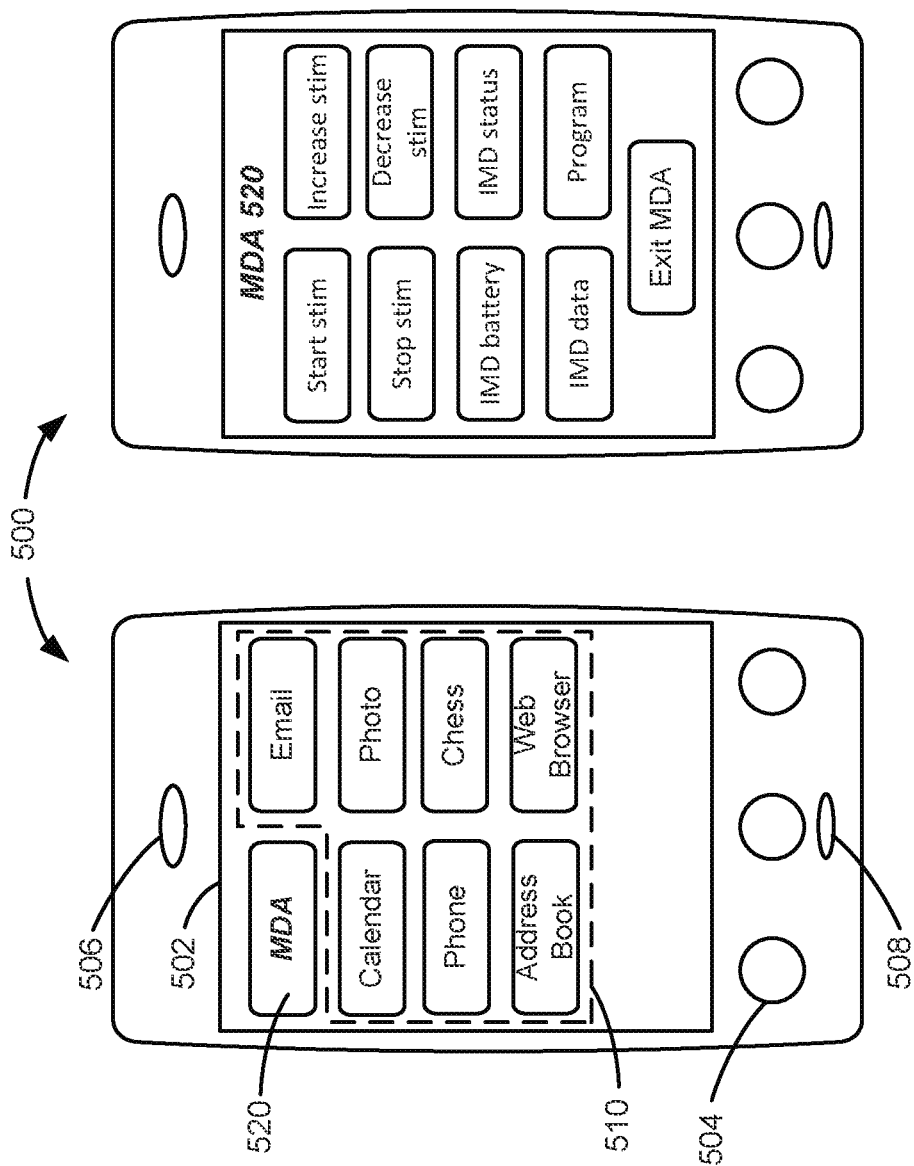
FIGS. 6A and 6B show embodiments a medical device application running on a hand-held portable external controller embodied as a mobile computing device.

FIGS. 6A and 6B show an example of a portable hand-held mobile device 500 configured for use as an external controller for an IMD, as described in commonly-owned U.S. Pat. No. 9,717,919, which is incorporated herein by reference. The mobile device 500 may be a commercial, multipurpose, consumer device, such as a cell phone, tablet, personal data assistant, laptop or notebook computer, or like device—essentially any mobile, hand-holdable device capable of functioning as a wireless external controller for an IMD. Examples include the Apple iPhone or iPad, Microsoft Surface, Nokia devices, Samsung Galaxy devices, and Google Android devices for example.

As shown in FIG. 6A, the mobile device 500 includes a user interface with a display 502, which may also receive input if it is a touch screen. The mobile device 500 may also have buttons 504 (e.g., a keyboard) for receiving input from the patient, a speaker 506, and a microphone 508. Shown on the display 502 is a typical home screen graphical user interface provided by the mobile device 500 when first booted or reset. A number of applications ("apps") 110 may be present and displayed as icons on the mobile device home screen, which the patient can select and execute.

One of the applications (icons) displayed in FIG. 6A is a Medical Device Application (MDA) 520, which when executed by the patient will configure the mobile device 500 for use as an external controller to communicate with an IMD. FIG. 6B shows the home screen of the MDA 520 after it is executed, which includes options selectable by a patient to control his stimulation program or monitor his IMD. For example, the MDA 520 may present options to: start or stop stimulation; increase or decrease the amplitude of the stimulation pulses (or adjust other pulse parameters and electrode settings); load/instantiate saved stimulation programs, check the battery and operating status of the IMD; review data telemetered from the IMD; exit the MDA 520 and return to the mobile device's home screen (FIG. 6A), etc. The MDA 520, like other applications 510 selectable in the mobile device 500, may have been downloaded using traditional techniques, such as from an Internet server or an "app store."

When the MDA 520 is first selected and executed, or when an appropriate selection is made in the MDA (FIG. 6B), wireless communications with the IMD can be established using a communication means in the mobile device 500 and enabled by the MDA 520. The above-incorporated '919 patent discloses different examples in which such communication can occur, illustrated here in FIGS. 7A-7B.

Figure 7B:
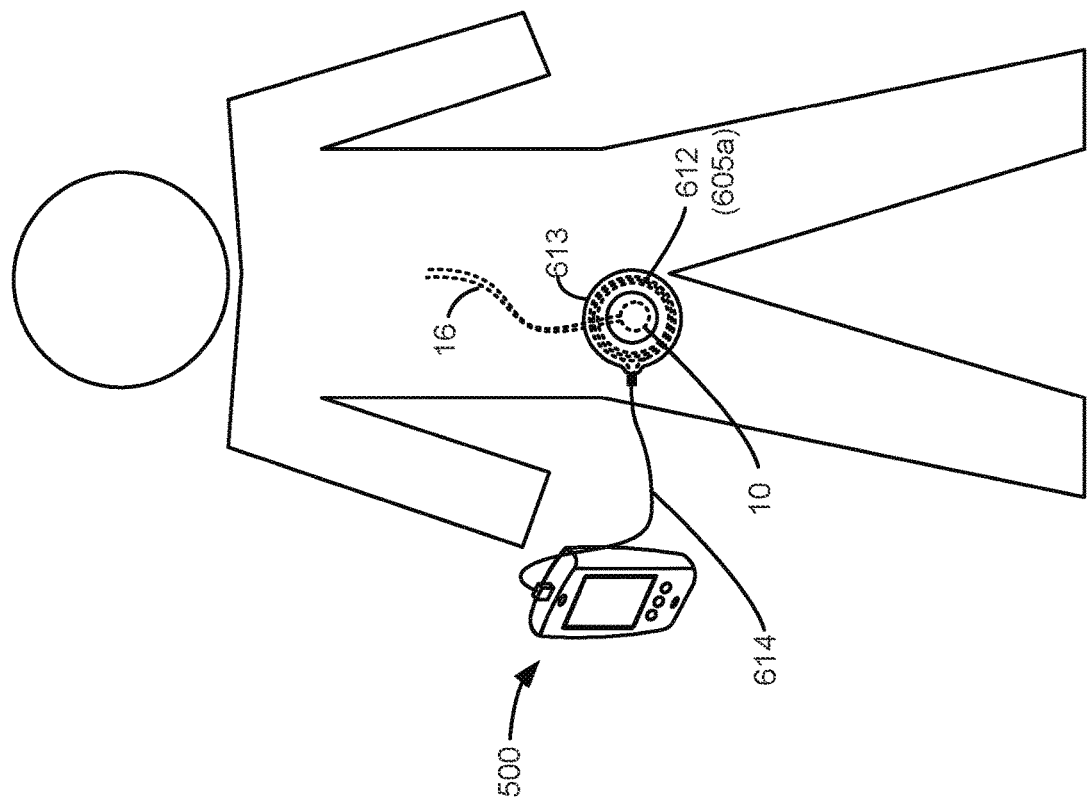
FIGS. 7A-7B show the use of a hand-held portable external controller embodied as a mobile computing device to communicate with an IPG.
Figure 7A:
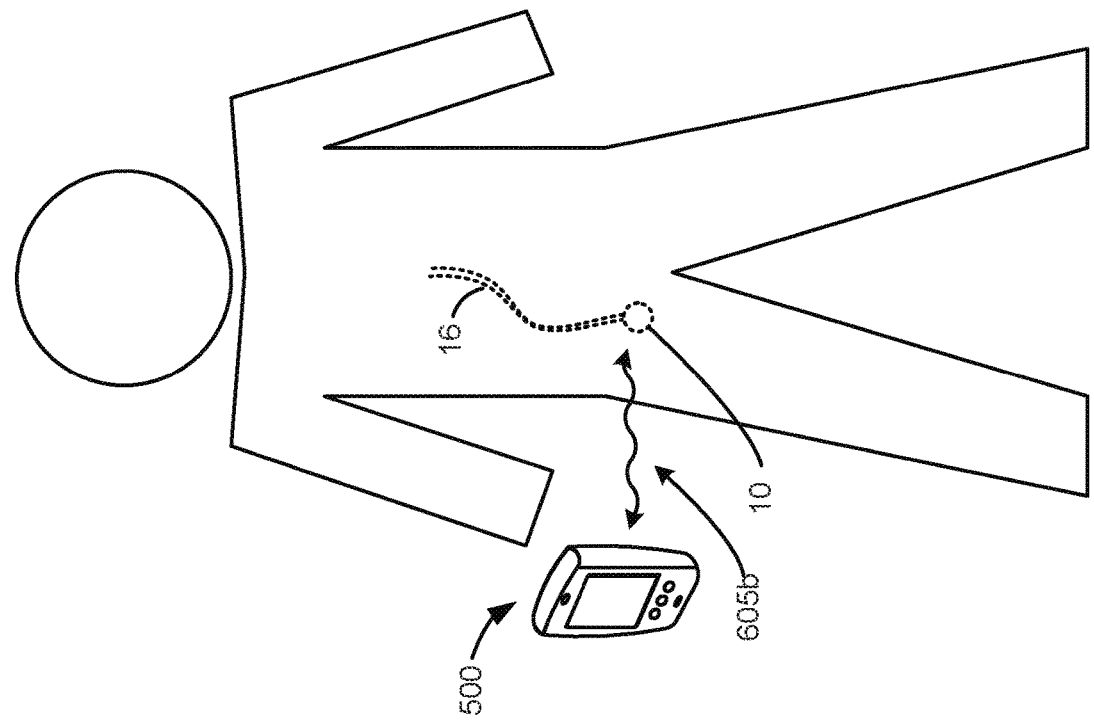

In FIG. 7A, the MDA 520 establishes wireless communication directly with the mobile device 500 along RF link 605b using short-range RF communication means supported by the mobile device 500 (e.g., Bluetooth). In this instance, the IMD 10 would include short-range communication means compatible with RF link 605b.

In FIG. 7B, a communication coil 612 in a communication head 613 is coupled by a cable 614 to a port on the mobile device 500, such as a USB port. In this instance, the communication coil 612 can be placed proximate to the IMD 10 to establish a magnetic induction link 605a, perhaps as modulated via frequency shift keying (FSK). The IMD 10 would include communication means compatible with magnetic induction link 605a (e.g., a coil antenna). The MDA 520 in this example would program the mobile device 500 to issue and receive data at its USB port, which data may be modulated or digital depending whether the modulation/demodulation circuitry resides in the mobile device 500 or the communication head 613.

As explained above, when a patient receives an implanted stimulator device (e.g., IPG) they undergo a fitting process with a clinician, whereby the clinician determines (1) which electrodes to use that best provide stimulation at the origination point of their pain (i.e., sweet-spot) and (2) what stimulation waveforms/neural dosage provides the best efficacy. Those parameters are stored in the patient's IPG. Some patients find that the programs stored in their IPG decrease in effectiveness over time or in certain situations. This may be due to several factors. For example, sometimes the electrode leads may shift over time. Other changes in effectiveness may be due to neuroplasticity of pain transmission pathways, cellular or fibrotic changes in the tissues around the electrodes, changes in patient pain tolerances, and the like. When a patient experiences such a decrease in therapeutic benefit, they are likely to return to the clinician to have their IPG reprogrammed. Often, the reprogramming session consists of small changes to the stimulation parameters. It also often occurs that decreases in therapeutic benefit are temporary and may be caused by factors such as the patient's activity or stress level, the weather, or may be due to the patient simply not using the correct neural dosage (i.e., stimulation intensity). In such instances, the patient might be better served either by waiting for a short period of time or by re-education concerning adjustment of the neural dosage, rather than by returning to the clinician for parameter re-adjustment.

Embodiments of the disclosure are directed to a set of tools that the patient can use to evaluate the effectiveness of the therapy provided by their IPG and for assisting the patient to conduct self-reprogramming in the case of loss of efficacy. The set of tools is collectively referred to herein as a reprogramming assistant (RA). The RA may be included as one or more functions within the patient's external controller 45. According to other embodiments, the RA may be included as one or more sub-routines within the medical device application (MDA) 520 of the patient's portable hand-held mobile device 500. Alternatively, the RA may be a stand-alone application within the patient's external controller 45 or mobile device 500. In the discussion that follows it is generally assumed that the aspects of the RA are implemented using a portable hand-held mobile device 500.

FIGS. 8A and 8B illustrate a logical overview of an embodiment of a reprogramming assistant (RA) and how it works to guide a patient if the efficacy of their treatment deteriorates. The illustrated RA includes two modules—an evaluation module (EM) and a reprogramming module (RPM). The EM is configured to evaluate and track the efficacy of the patient's therapy, for example, based on ratings provided by the patient. The EM may also be configured for one or more data gathering functions, for example, to gather data related to key factors that may influence the patient's therapy and efficacy, such as neural dosage, activity, mood (e.g., stress), and weather. If the EM determines that the patient's efficacy has decreased, the EM can use data entered by the patient to determine whether the decrease is likely due to an external factor, such as the patient's activity, weather, mood, etc. In such instances, the EM may determine that reprogramming is not warranted. The EM may also determine whether the decrease in efficacy is due to an incorrect neural dosage of stimulation. In such instances, the patient may be provided with a user interface that guides the patient to adjust their neural dosage. The EM may also determine that the loss of efficacy is due to a mismatch of the stimulation location and the origination point of the patient's pain. If that is the case, then a reprogramming module (RPM) may be launched and the patient may be guided through steps for reprogramming their IPG to recover the correct stimulation location.

If it is determined that reprogramming is warranted, then the RPM guides the patient through a decisional tree, based on patient input, for reprogramming their stimulation location. The RM may include one or more pre-loaded "rescue programs" and may instruct the patient on how to activate them. For example, the based on patient preferences, the patient may select a rescue program that is based on paresthesia or one that is sub-perception. Ultimately, if the patient is unable to address the loss of efficacy by self-reprogramming, the RM may instruct the patient to schedule a clinical visit. Each of these aspects of the EM and RPM are discussed in more detail below.

Figure 9:
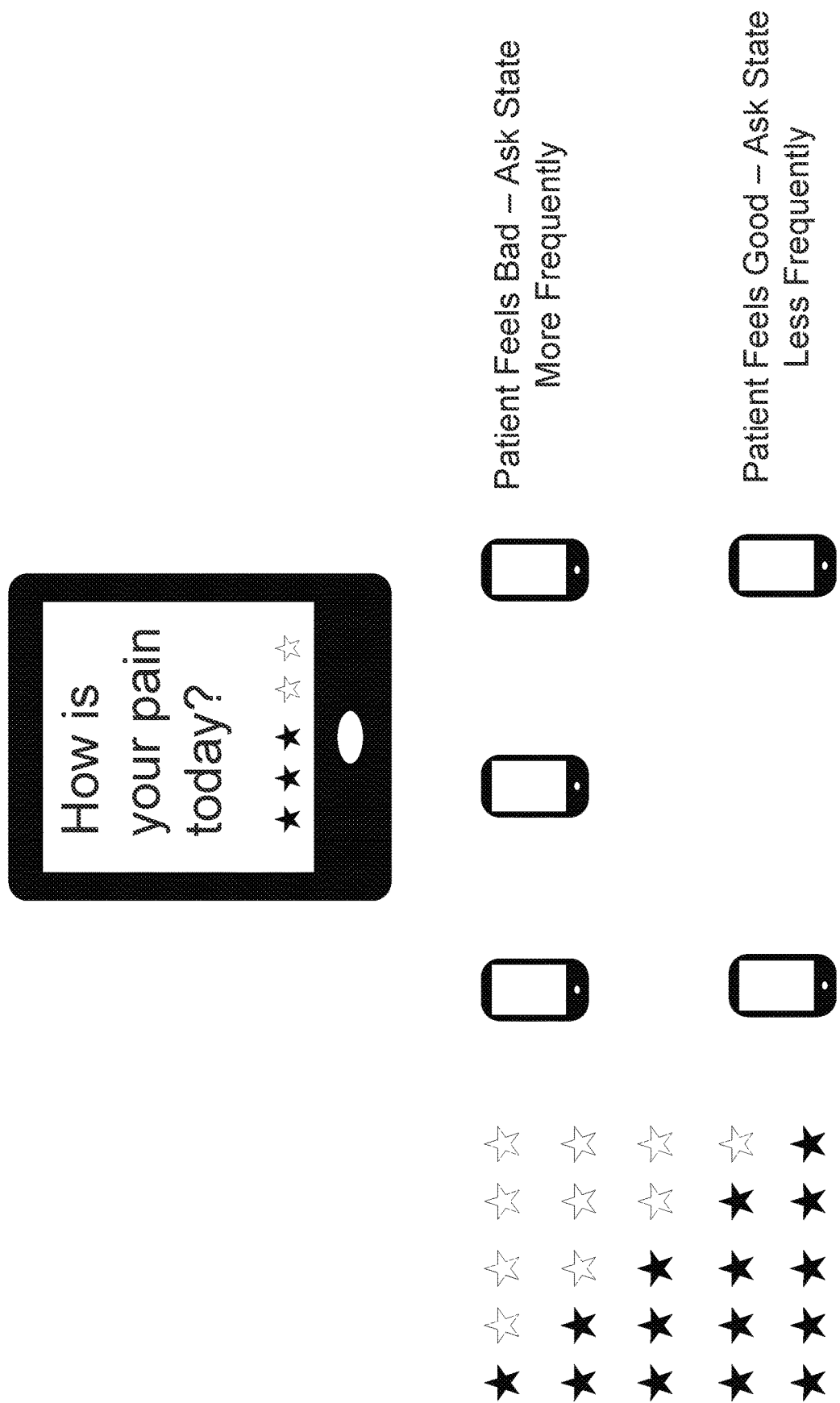
FIG. 9 shows aspects of an evaluation module (EM).

FIG. 9 illustrates an example of how the evaluation module (EM) can evaluate the efficacy of a patient's therapy. Periodically the EM can prompt the patient for feedback relating to their therapy or pain level. In the illustrated example, the EM prompts the patient to rate their pain based on a scale of one to five stars, wherein one star indicates that their therapy is ineffective or their pain is severe and five stars indicates that the therapy is very effective and their pain level is readily tolerable. Other ranking schemes may be used, such as numerical rankings, smile/frown icons, and the like. The EM can prompt for an efficacy evaluation more often if the patient consistently ranks their therapy as ineffective and less often if the patient ranks their therapy as effective, thereby minimizing intrusion into the patient's time. According to some embodiments, the EM may prompt for an efficacy evaluation based on factors such as weather, patient activity, or the like. Such periodic querying of the patient regarding the efficacy of their therapy (i.e., their pain levels) is useful whether the patient's therapy is supra-perception or sub-perception.

Figure 10:
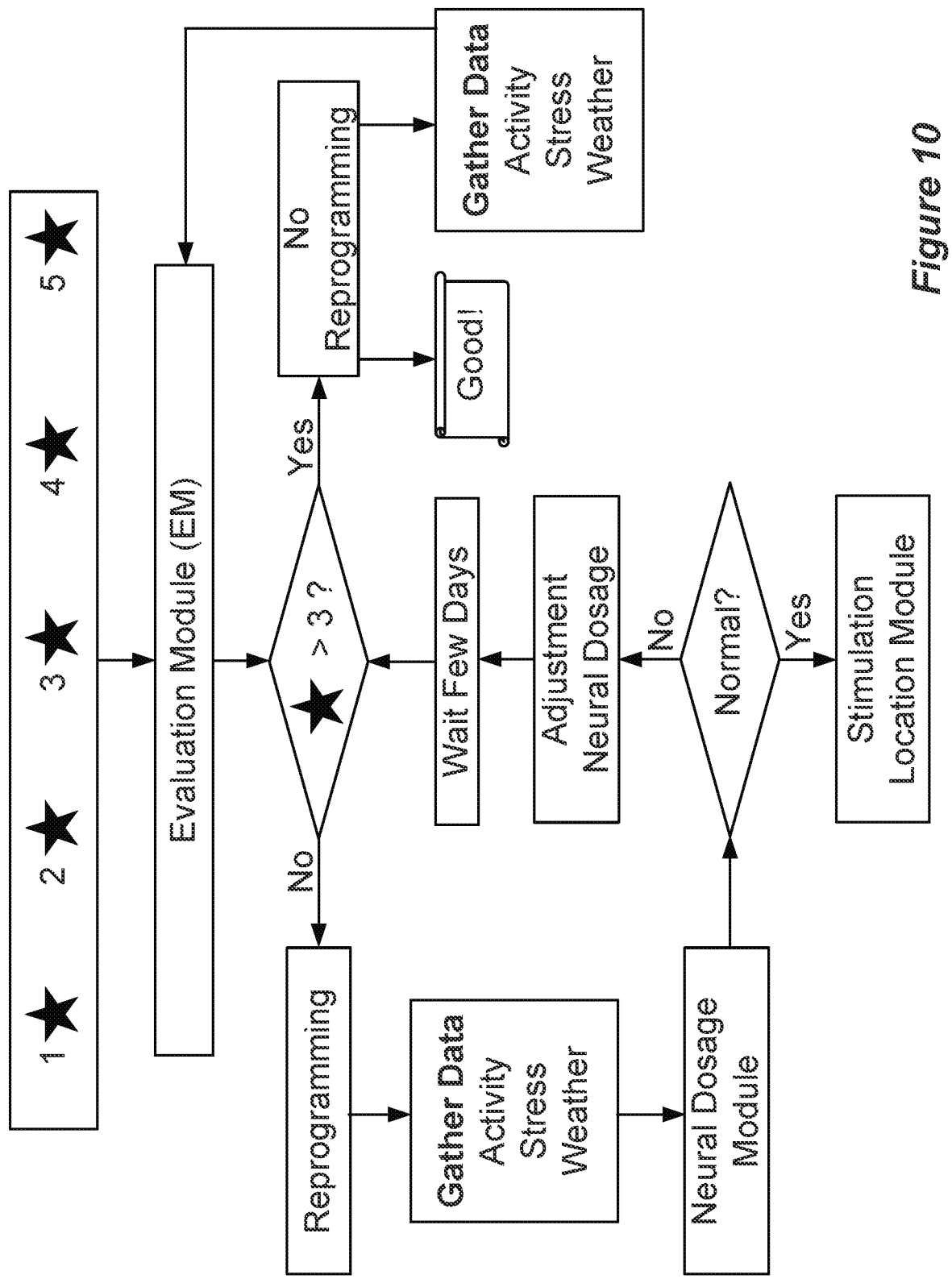
FIG. 10 shows aspects of an implementation of an evaluation module (EM).

FIG. 10 illustrates a decision tree that the EM can use to evaluate whether reprogramming is warranted, based on the patient's efficacy rating (i.e., pain level rating). The EM can receive one or more efficacy ratings and determine if the efficacy rating (i.e., number of stars) exceeds a certain threshold (3 stars in the illustrated embodiment). It should be noted that the efficacy rating threshold may be set to a value other than 3; 3 is just an example. If the efficacy rating exceeds the threshold, then the EM determines that the therapy is satisfactory and that reprogramming is not necessary. The EM may post an acknowledgement message to the user. The EM may also gather data relating to factors that might influence the efficacy of the patient's therapy, such as the patient's activity level, stress level, weather, etc. The EM may ask the patient questions prompting the patient to enter information relating to such factors. Additionally, or alternatively, the EM may obtain information about such factors from sensing devices such as a heartrate monitor, smart wearable devices, etc. According to some embodiments, information to the weather may be downloaded from the internet, for example. The gathered data may feed back to the EM so that efficacy can be better correlated with such factors.

If the efficacy rating is below the threshold, then the EM may launch a reprogramming subroutine. According to some embodiments, the EM may require multiple consistent efficacy ratings below the threshold before instantiating reprogramming, for example, to avoid reprogramming simply because the patient is having a "bad day." If the required number of low efficacy ratings are received, then the EM may perform one or more preliminary checks to further evaluate whether reprogramming should be attempted. For example, the EM may gather data related to the patient's activity level, stress level, the weather, etc., as described above. Additionally/alternatively, the EM may query the neural dosage of stimulation that the patient is receiving. If any of these factors are unexpected or abnormal, the EM may determine that stimulation reprogramming to change the stimulation location is not warranted at this time. Instead, the patient may be instructed to take other corrective measures, such as adjusting their neural dosage (volume of stimulation). Adjustment of neural dosage is described in more detail below. According to some embodiments, the patient may be provided, via a GUI on their external device 500, instructions and controls (such as a slider bar) for adjusting their neural dosage. Moreover, the patient may be provided with tips, such as recommended neural dosages for their situation, for example 50% volume during the day and 20% volume during sleeping hours. According to some embodiments, the patient may be directed to educational material (on the internet, for example) explaining the effects of stress, activity, weather, etc., as such factors relate to their condition. Once appropriate adjustments are made, and such information is transmitted to the patient, the patient may be instructed to wait a few days and to re-rank the efficacy of their therapy. If the information garnered in the preliminary checks (i.e., neural dosage, stress, activity, weather, etc.) are all within normal or expected bounds, then the EM may determine that reprogramming of the stimulation location is indeed warranted and may launch the reprogramming module (RPM), which will help guide the patient through reprogramming their IPG.

FIG. 11 illustrates exemplary modules (algorithms) that the reprogramming assistant may use to adjust one or more aspects of a patient's therapy. Some or all these exemplary modules may be available or unavailable to a patient depending on the patient's competence and confidence regarding self-reprogramming of their IPG.

The illustrated embodiment of the reprogramming assistant is based on the assumption that loss/decrease of efficacy in a patient's stimulation may be caused by one or both of (1) a misalignment of the stimulation location with the neural elements giving rise to the patient's pain, and/or (2) a problem with the neural dosage (i.e., the stimulation parameters such as frequency, pulse width, and amplitude) of the stimulation. Thus, the reprogramming assistant includes a stimulation location module, which comprises one or more algorithms for adjusting the location at which stimulation is applied and a neural dosage module, which allows for the adjustment of neural dosage.

As explained further below, in some instances, supra-perception stimulation may be used for reprogramming the patient's stimulation and in other instances, sub-perception stimulation may be used for reprogramming. For example, the patient may prefer one or the other of supra- or sub-perception. Thus, the reprogramming assistant may include paresthesia-based algorithms and sub-paresthesia-based algorithms for adjusting the stimulation location. An example of a paresthesia-based reprogramming module (algorithm) is the paresthesia rescue locations (PRL) module. The PRL may invoke a schedule of pre-loaded programs of stimulation parameters that provide supra-perception stimulation to different locations. Using a GUI on their external controller, the patient can indicate if one of the pre-loaded rescue locations overlap with their pain. Another example of a paresthesia-based reprogramming module (algorithm) is the center point of stimulation module (CPSM). The CPS module (CPSM) is a module that allows the patient to manually adjust/move the CPS using steering algorithms to better cover their pain. When the CPSM is invoked, the patient may be provided with a GUI by which they can move the CPS and be provided with instructions for moving the CPS.

In some cases, sub-perception stimulation may be used during reprogramming of the stimulation location. An example of a module (algorithm) that may use sub-perception stimulation is the anatomical location schedule (ALS). The anatomical location schedule (ALS) is a schedule of preprogrammed stimulation programs that provide stimulation (typically sub-perception stimulation) directed to different anatomical locations. By cycling through preprogrammed anatomical locations, the patient may find a location that effectively treats their pain.

As mentioned above, loss in efficacy may be due to improper neural dose of stimulation. Moreover, in cases when the location of stimulation is reprogrammed, the patient may also need to adjust their neural dose at the new location. Thus, the reprogramming assistant provides modules (algorithms) for adjusting neural dose. Again, in some instances, the neural dose of sub-perception stimulation may be adjusted and in other neural dose instances supra-perception stimulation may be adjusted. In both cases, the patient may be provided with a GUI page having a controller for adjusting neural dose. For example, the GUI page may include a slider bar or some other control element. According to some embodiments, the patient may be constrained as to the parameter values they may change to adjust neural dose. For example, for paresthesia-based (i.e., supra-perception) stimulation, the neural dose adjustment may be constrained to lower frequencies (i.e., about 40-100 Hz) and the amplitudes may be kept above the perception threshold. For adjusting sub-perception stimulation, the neural dose adjustments may be unconstrained as to frequencies, but the neural dosage may be constrained to known relationships of parameter values (e.g., frequency, pulse width and/or amplitude) which are known to provide sub-perception therapy. Such known relationships are discussed in more detail below.

Figure 12:
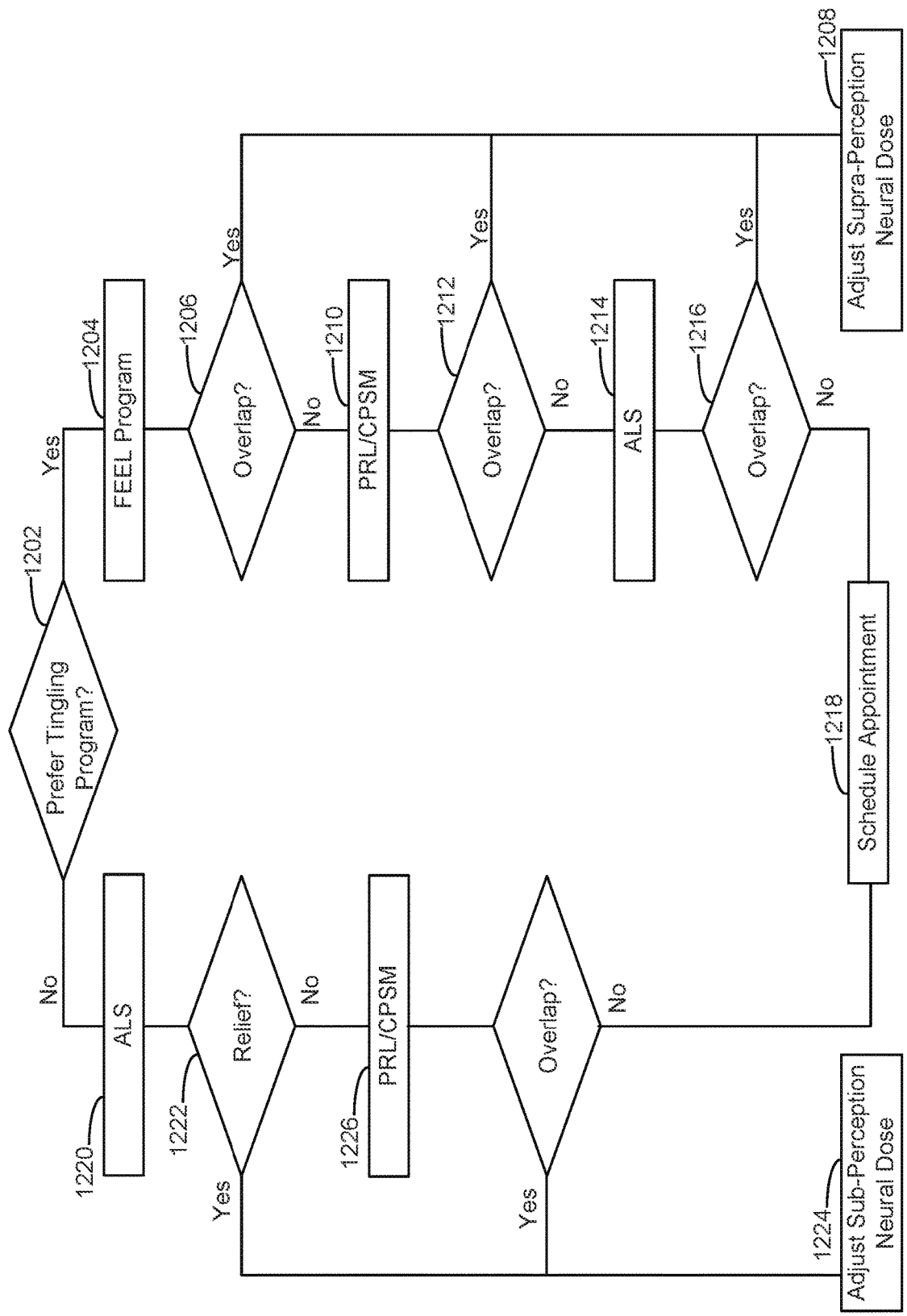
FIG. 12 shows an embodiment of how components of a reprogramming module (RPM) are stored in memory locations of an IPG.

FIG. 12 illustrates one example of how the supra-perception reprogramming options (PRL and/or CPSM) and the sub-perception reprogramming option (ALS) may be implemented to help a patient recover the correct center point of stimulation (CPS) in the event of loss in efficacy. Assume that the efficacy of the patient's therapy has been consistently ranked as unsatisfactory and that the preliminary checks have determined that the loss in efficacy is not due to factors such as insufficient neural dosage, stress, activity, weather, etc. The reprogramming module (algorithm) may be launched to help the patient recover the correct CPS. The patient may be asked 1202 if they prefer to attempt reprogramming using sub-perception of supra-perception. For example, they may be asked if they "prefer a tingling program."

If the patient chooses to use supra-perception, a FEEL program may be launched 1204. The FEEL program is a program that may present one or more GUI pages on the patient's external device 500 which allows the patient to indicate if and where they sense paresthesia and indicate if the paresthesia overlaps with their pain. FIG. 13 illustrates one example of such a GUI. In FIG. 13, the patient is presented with a first page 1302 that lets the patient indicate where they are experiencing pain and a second page 1304 that lets the patient indicate where they sense paresthesia. Using pixel processing, the FEEL program can determine if the paresthesia adequately overlaps with the patient's pain (FIG. 12, 1206).

Referring again to FIG. 12, if adequate paresthesia/pain overlap is indicated, then it may be determined that attempting to move the stimulation location is not warranted. In that case, the neural dosage (supra-perception) may be adjusted 1208. Adjustment of neural dosage is discussed in more detail below. If adequate paresthesia/pain overlap is not indicated, then the patient may be prompted and guided to reprogram their stimulation to move the center point of stimulation using the paresthesia rescue location schedule (PRL) and/or the center point of stimulation module (CPSM) 1210.

Figure 14:
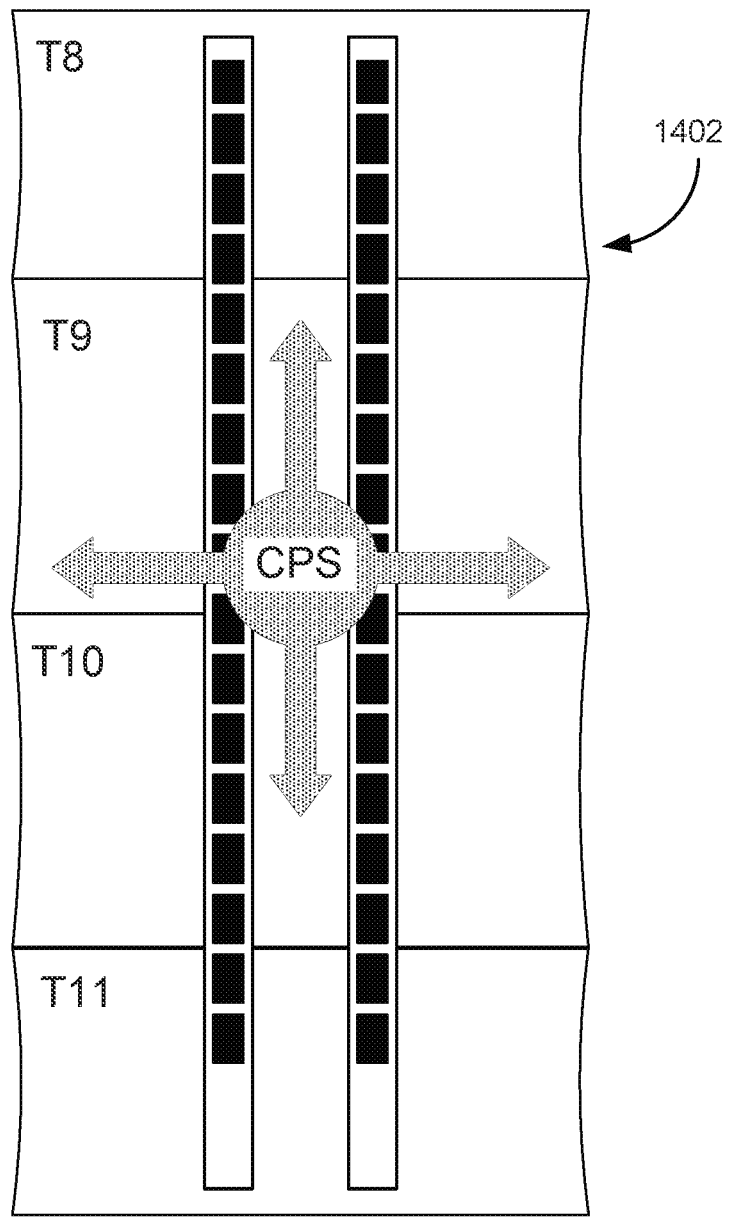
FIG. 14 shows an implementation of center point of stimulation (CPS) rescue locations.

According to some embodiments, the paresthesia rescue location (PRL) schedule comprises a schedule of pre-programmed stimulation parameters that give rise to different center points of stimulation (CPSs). For example, the PRL may include four programs. Each of the stimulation parameter programs may cause CPS locations that are some distance from the original CPS, as illustrated in FIG. 14. For example, the rescue paresthesia locations may be located 10 mm rostral and caudal of the original CPS and 2 mm in either mediolateral direction from the original CPS. Note that these distance values are exemplary only. When the PRL schedule is launched, program scheduling is used to cycle through the CPS programs and hold each CPS for a period of time. For example, each program may be run for several minutes (e.g., 1-5 minutes). Program scheduling is described, for example, in U.S. Pat. No. 9,895,545, the contents of which are hereby incorporated by reference. After each program is run, the patient may be asked to indicate if paresthesia evoked at the new stimulation location overlaps with their pain.

According to some embodiments, the patient may be given the option to attempt a manual sweet-spot search using the CPS module CPSM. The CPSM algorithm provides a guided paresthesia-based sweet-spot search algorithm. The CPSS may employ paresthesia-based sweet-spot searching, for example, as described in the above-incorporated '282 Patent. If the CPSM is launched, the patient may be presented with a GUI image, such as illustrated in FIG. 14, whereby the patient can use arrows to move the desired location at which they would like the paresthesia to occur. Alternatively, the patient may be presented with a GUI image, such as illustrated in FIG. 13, where the patient can indicate where they would like to feel paresthesia or they may be presented with arrows that the patient can use to indicate which way to move the CPS. Response to the patient's GUI instructions, the reprogramming algorithm may use current steering to move the CPS. Stimulation steering is described in U.S. Patent Application Publication No. 2018/0056068, the contents of which are incorporated herein by reference.

Figure 15B:
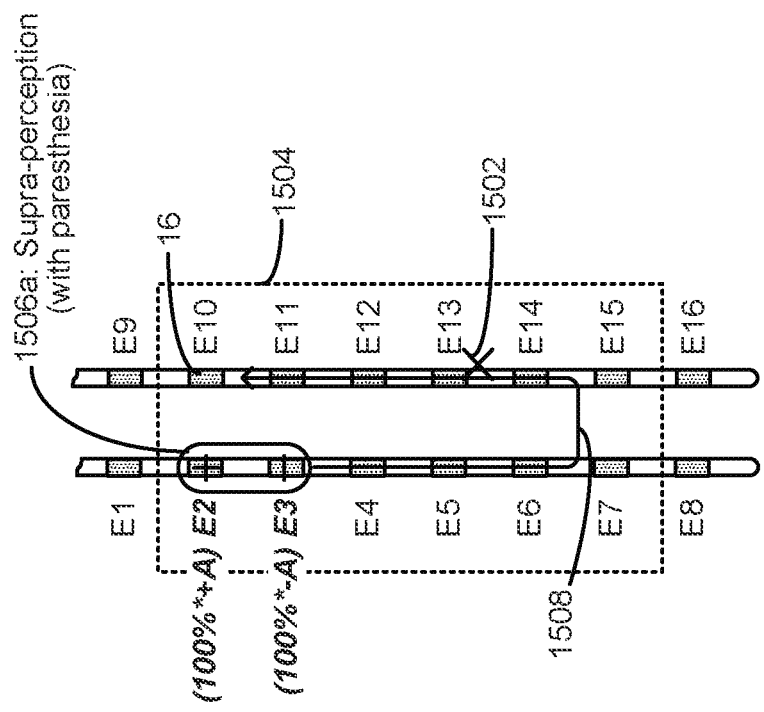
Figure 15A:
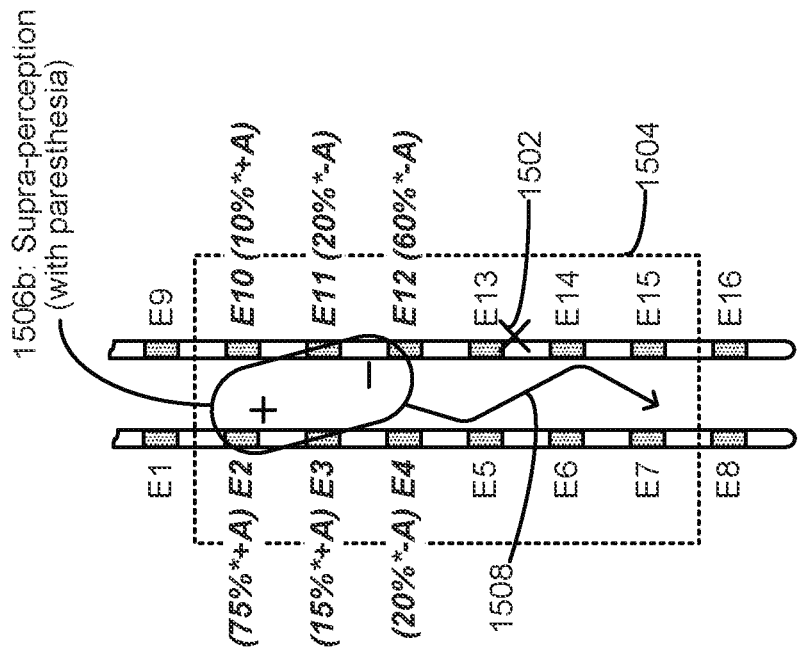

FIGS. 15A-15D illustrate examples of sweet-spot searching as may be conducted using the CPSM. In the example shown, it is assumed that a pain site 1502 is likely within a tissue region 1504. In the example shown, region 1504 is bounded by electrodes E2, E7, E15, and E10. In FIG. 15A, when the CPSM routine is initiated, a supra-perception trial bipole 1506a is selected, in which one electrode (e.g., E2) is selected as an anode that will source a positive current (+A) to the patient's tissue, while another electrode (e.g., E3) is selected as a cathode that will sink a negative current (−A) from the tissue. This is similar to what was illustrated earlier with respect to FIG. 2, and biphasic stimulation pulses can be used employing active charge recovery. After the bipole 1506a is tested at this first location, the patient may be asked if the paresthesia covers their pain. If the answer is yes, then the trial bipole 1506a is used to for ongoing therapy 1320. If the trial bipole does not produce paresthesia that covers the patient's pain, then a different combination of electrodes is chosen (anode electrode E3, cathode electrode E4), which moves the location of the trial bipole 1506a in the patient's tissue. The patient may be instructed to try another electrode combination. Again, the amplitude of the current A may need to be adjusted to an appropriate supra-perception level. In the example shown, the bipole 1506a is moved down one electrode lead, and up the other, as shown by path 1508 in the hope of finding a combination of electrodes that covers the pain site 1502. After each trial application of the bipole 1506a, the patient may be asked if correct paresthesia coverage is obtained. In the example of FIG. 15A, given the pain site 1502's proximity to electrodes E13 and E14, it might be expected that a bipole 1506a at those electrodes will provide the best relief for the patient, as reflected by the patient's feedback. According to some embodiments, the patient may be provided with arrows or other indicators that the patient can use to move the bipole 1506a, rather than having to sequentially follow the path 1508.

Figure 16:
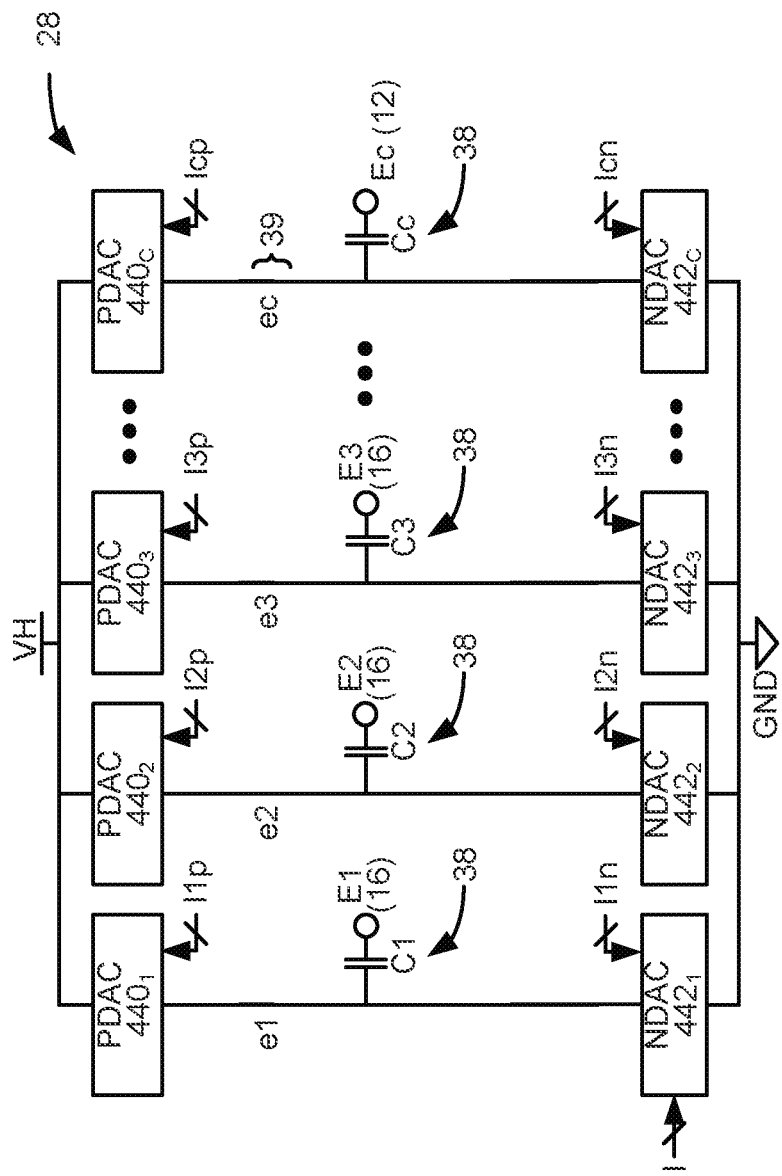
FIG. 16 shows circuitry for multiple independent current control (MICC).

FIGS. 15B-15D show other supra-perception bipoles 1506b-1506d that may be used, and in particular show how the virtual bipoles may be formed using virtual poles by activating three or more of the electrodes 16. Virtual poles are discussed further in U.S. Pat. No. 10,881,859, which is incorporated herein by reference in its entirety, and thus virtual poles are only briefly explained here. Forming virtual poles is assisted if the stimulation circuitry 28 used in the IPG is capable of independently setting the current at any of the electrodes—what is sometimes known as a Multiple Independent Current Control (MICC), which is explained further below with reference to FIG. 16.

When a virtual bipole is used, the CPSM may define an anode pole (+) and a cathode pole (−) at positions to form a virtual bipole 1506b (FIG. 15B). The anode pole and cathode pole may not necessarily correspond to the position of the physical electrodes 16. For example, in FIG. 15B, the virtual anode pole is located between electrodes E2, E3 and E10. The CPSM may then calculate based on this position that each of these electrodes (during first pulse phase 30a, FIG. 2) will receive an appropriate share (X %) of the total anodic current+A to locate the virtual anode at this position. Since the virtual anode's position is closest to electrode E2, this electrode E2 may receive the largest share of the specified anodic current+A (e.g., 75%*+A). Electrodes E3 and E10 which are proximate to the virtual anode pole's position but farther away receive lesser shares of the anodic current (e.g., 15%*+A and 10%*+A respectively). Likewise, it can be seen that from the designated position 1510 of the virtual cathode pole, which is proximate to electrodes E4, E11, and E12, that these electrodes will receive an appropriate share of the specified cathodic current −A (e.g., 20%*−A, 20%*−A, and 60%*−A respectively, again during the first pulse phase 30a, FIG. 2). These polarities would then be flipped during the second phases 30b of the pulses. In any event, the use of virtual poles in the formation of bipole 1506b allows the field in the tissue to be shaped, and many different combinations of electrodes can be tried during the sweet spot search. In this regard, it is not strictly necessary that the (virtual) bipole be moved along an orderly path 1508 with respect to the electrodes, and the path may be randomized, perhaps as guided by feedback from the patient.

FIG. 15C shows a useful virtual bipole 1506c configuration that can be used during the sweet spot search. This virtual bipole 1506c again defines a target anode and cathode whose positions do not correspond to the position of the physical electrodes. The virtual bipole 1506c is formed along a lead-essentially spanning the length of four electrodes from E1 to E5. This creates a larger field in the tissue better able to recruit the patient's pain site 1502. This bipole configuration 301c may need to be moved to a smaller number of locations than would a smaller bipole configuration compared to 1506a of FIG. 15A as it moves along path 1508, thus accelerating pain site 1502 detection. FIG. 15D expands upon the bipole configuration of FIG. 15C to create a virtual bipole 1506d using electrodes formed on both leads, e.g., from electrodes E1 to E5 and from electrodes E9 to E13. This bipole 1506d configuration need only be moved along a single path 1508 that is parallel to the leads, as its field is large enough to recruit neural tissue proximate to both leads. This can further accelerate pain site detection.

It should be noted that in the examples illustrated in FIGS. 15A-15D, bipoles (including virtual bipoles) were illustrated. However, other "pole configurations," such as tripoles and other multipoles are also possible, and such pole configurations may include virtual pole configurations. As used herein, the term "pole configuration" refers to combinations of electrodes implemented to produce electrical poles, such as bipoles, tripoles, and the like, including virtual bipoles, tripoles, etc.

As mentioned above, the creation of virtual bipoles, such as illustrated in FIGS. 15B-15D, can be accomplished using Multiple Independent Current Control (MICC) capabilities of the IPG. Multiple Independent Current Control (MICC) is explained in one example with reference to FIG. 16, which shows the stimulation circuitry 28 (FIG. 1) in the IPG used to form prescribed stimulation at a patient's tissue. The stimulation circuitry 28 can control the current or charge at each electrode independently allows the current or charge to be steered to different electrodes, which is useful for example when moving the bipole 1506i along path 1508 during the sweet spot search (FIG. 15A-15D). The stimulation circuitry 28 includes one or more current sources $440_i$ and one or more current sinks $442_i$. The sources and sinks $440_i$ and $442_i$ can comprise Digital-to-Analog converters (DACs), and may be referred to as PDACs $440_i$ and NDACs $442_i$ in accordance with the Positive (sourced, anodic) and Negative (sunk, cathodic) currents they respectively issue. In the example shown, a NDAC/PDAC $440_i/442_i$ pair is dedicated (hardwired) to a particular electrode node ei 39. Each electrode node ei 39 is preferably connected to an electrode Ei 16 via a DC-blocking capacitor Ci 38, which act as a safety measure to prevent DC current injection into the patient, as could occur for example if there is a circuit fault in the stimulation circuitry 28 or 44. PDACs $440_i$ and NDACs $442_i$ can also comprise voltage sources.

Proper control of the PDACs $440_i$ and NDACs $442_i$ allows any of the electrodes 16 and the case electrode Ec 12 to act as anodes or cathodes to create a current through a patient's tissue. Such control preferably comes in the form of digital signals Iip and Iin that set the anodic and cathodic current at each electrode Ei. If for example it is desired to set electrode E1 as an anode with a current of +3 mA, and to set electrodes E2 and E3 as cathodes with a current of −1.5 mA each, control signal I1p would be set to the digital equivalent of 3 mA to cause PDAC $440_1$ to produce +3 mA, and control signals I2n and I3n would be set to the digital equivalent of 1.5 mA to cause NDACs $442_2$ and $442_3$ to each produce −1.5 mA. Note that definition of these control signals can also occur using the programmed amplitude A and percentage X % set. For example, A may be set to 3 mA, with E1 designated as an anode with X=100%, and with E2 and E3 designated at cathodes with X=50%. Alternatively, the control signals may not be set with a percentage, and instead the current that will appear at each electrode at any point in time can be prescribed.

In short, the current at each electrode, or to steer the current between different electrodes can be independently set. This is particularly useful in forming virtual bipoles, which as explained earlier involve activation of more than two electrodes. MICC also allows more sophisticated electric fields to be formed in the patient's tissue.

Other stimulation circuitries 28 can also be used to implement MICC. In an example not shown, a switching matrix can intervene between the one or more PDACs $440_i$ and the electrode nodes ei 39, and between the one or more NDACs $442_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, 10,962,097, and U.S. Patent Application Publications 2018/0071513 and 2018/0071520.

Much of the stimulation circuitry 28, including the PDACs $440_i$ and NDACs $442_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with the IPG's telemetry antennas), circuitry for generating the compliance voltage VH that powers the stimulation circuitry, various measurement circuits, etc.

Referring again to FIG. 12, the patient can be queried to determine if paresthesia overlap was obtained using either the PRL schedule or the CPSM 1212. If paresthesia overlap is obtained, then the new center point of stimulation (CPS) can be used for ongoing therapy and the patient can be guided to adjust their neural dose 1208. If paresthesia overlap is not obtained, then the patient may be directed to use the anatomical location schedule (ALS) 1214.

The anatomical location schedule (ALS) is a schedule of stimulation programs, each configured to provide large contoured stimulation field shapes to different anatomical regions. For example, FIG. 17 illustrates a representation of a portion of the patient's anatomy (T8-T11 vertebrae in the illustration). The portion is divided into five anatomical locations, 1702A-1702E. Each of the anatomical locations 1702A-1702E contain about 5 electrodes 16. The ALS may comprise programs, each of which are configured to provide stimulation to one of the anatomical locations 1702A-1702E. FIG. 18 illustrates one embodiment of how the electrodes contained within the anatomical location 1702A can be fractionalized to provide a virtual bipole 1802 that covers the anatomical location 1702A.

Program scheduling can be used to cycle through each programs of the ALS, thereby sequentially applying stimulation to the locations 1702A-1702E. Each program may be maintained for a specified time period before cycling to the next program. If the programs in the ALS provide subperception therapy, each program may be run for a number of days (e.g., 1-5 days) before cycling to the next program. If the programs provide supra-perception therapy, then each program may be run for a few minutes (e.g., 1-5 minutes) before cycling to the next program. In this case, since the patient has elected to use super-perception reprogramming, the ALS may sequentially provide supra-perception therapy to each of the locations 1702A-1702E for a few minutes. Referring again to FIG. 12, after each program in the ALS is run, the patient may be asked in the paresthesia overlaps with their pain 1216. If one of the stimulation programs is identified that produces overlapping paresthesia, then the neural dosage may be adjusted 1208 and the stimulation used for continuing therapy. If none of the programs provide overlapping paresthesia, then the patient may be instructed to schedule an appointment with a clinician 1218. Note here that the ALS may be run in a manner that provides sub-perception therapy. As mentioned above, if sub-perception therapy is used, then each program of the ALS may be run for days rather than only minutes. If a program is found that provides pain relief to the patient, then a location corresponding to that program can be used to provide supra-perception therapy after increasing the neural dose.

Returning to the top of FIG. 12, the patient may select to use sub-perception therapy 1202 for reprogramming their IPG to recover the correct stimulation location. In that case, the patient may be guided through the process of running the ALS. According to some embodiments, when the ALS is invoked, sub-perception stimulation is applied to the first anatomical location (e.g., 1702A). After some time (e.g., 1-5 days), the patient is asked to rank the efficacy of that stimulation. Then sub-perception therapy is applied to the next anatomical location (e.g., 1702B) and after a period of time the patient is asked to rank that therapy. The process is continued for each of the anatomical locations. The ALS can identify the anatomical location therapy that the patient ranks as having the highest efficacy. The patient can be asked if that therapy provides adequate pain relief 1222. If adequate pain relief is obtained, therapy can be continued using the stimulation settings determined using the ALS or the neural dose for sub-perception therapy may be further adjusted 1224.

If the patient fails to recover the correct location for stimulation using the ALS, the patient may be prompted to use the supra-perception methods (PRL and/or CPSM) to attempt to recover the correct stimulation location 1226. Those methods may be implemented as described above. Note that implementing the supra-perception methods may involve implementing the FEEL module, as described above. If the patient is successful at recovering the correct stimulation location using the PRL and/or CPSM, then sub-perception therapy can be used at the new location after adjusting the neural dose 1224. If attempts to recover the correct stimulation location fail, then the patient may be instructed to schedule an appointment with a clinician 1218.

Figure 19:
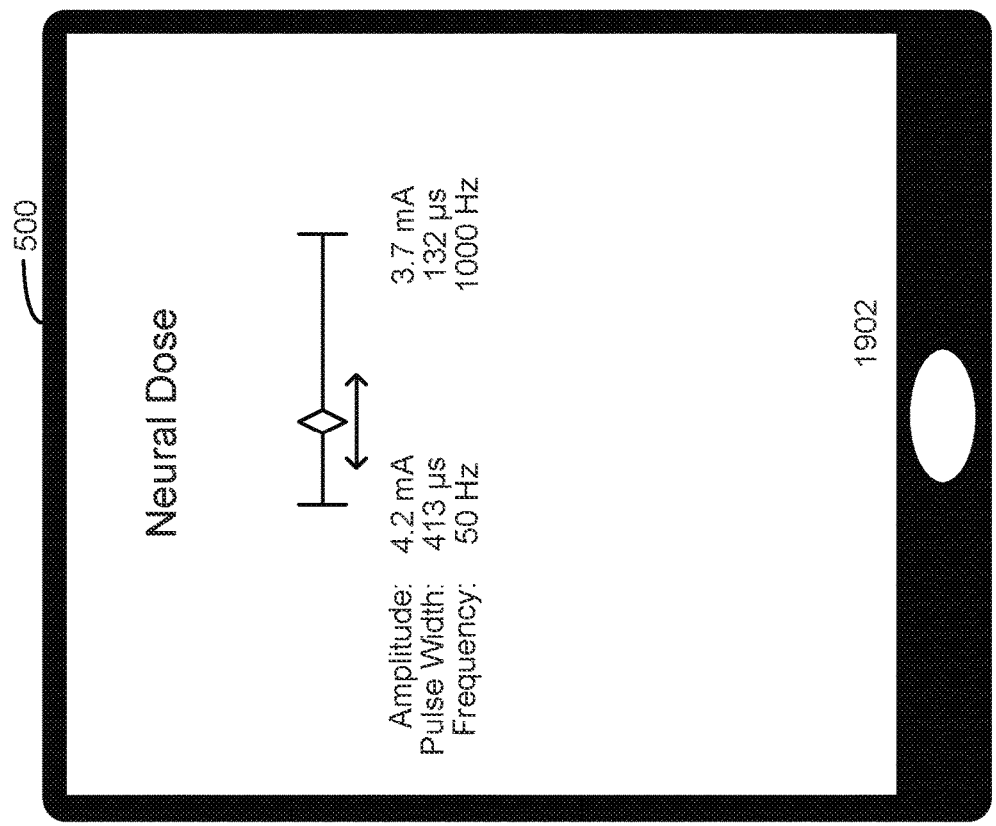
FIG. 19 shows a GUI for controlling neural dosage.

Once the correct stimulation location is recovered using any of the techniques described with respect to FIG. 12, it may be necessary to adjust the neural dosage (amplitude, pulse width and/or frequency) of the stimulation (e.g., 1208/1224 of FIG. 12). According to some embodiments, the amplitude, pulse width and frequency is adjusted in accordance with relationships, which have been shown to provide therapeutic benefits. Examples of such relationships are described in the above-incorporated '282 Patent. For example, FIG. 19 shows the relationship between frequency and pulse width at which effective sub-perception therapy was reported by patients for frequencies of 10 kHz and below. Likewise, concurrently filed and co-owned U.S. Patent Application Publication 2020/0009367 (herein "the '367 Publication"), which is hereby incorporated herein by reference in its entirety, describes improved sub-perception modeling that incorporates relationships between pulse width, frequency and perception threshold. As explained in that application, the perception threshold is useful to add as a variable to modeling because it varies from patient to patient. Some patients will have electrodes closer to or farther from the spinal neural fibers and therefore will experience sub-perception at differing amplitudes of current. By including perception thresholds in the modeling sub-perception can be measured for each patient with the modeling able to provide an optimal amplitude for sub-threshold stimulation in addition to frequency and pulse width. In other words, an ideal range of pulse width, frequency, amplitudes that provide sub-perception therapy is provided by that application.

According to some embodiments, the patient may be provided with a GUI page 1902 as illustrated in FIG. 19 for adjusting the neural dosage provided by the stimulation. As the slider 1904 is adjusted, the amplitude, pulse width, and frequency are adjusted on a continuum predicted by the modeling described in the above-incorporated '367 Publication to provide effective sub-perception therapy.

Various aspects of the disclosed techniques, including processes implementable in the IPG, or in external devices such as the external controller (e.g., personal computing device 500) can be formulated and stored as instructions in a computer-readable media associated with such devices, such as in a magnetic, optical, or solid-state memory. The computer-readable media with such stored instructions may also comprise a device readable by the or external controller, such as in a memory stick or a removable disk, and may reside elsewhere. For example, the computer-readable media may be associated with a server or any other computer device, thus allowing instructions to be downloaded to the external controller or to the IPG, via the Internet for example.

Note that some of the applications to which this present disclosure claims priority, which are incorporated by reference above, are directed to concepts (e.g., selecting optimal stimulation parameters, and in particular stimulation parameters that cause sub-perception at lower frequencies) that are relevant to what is disclosed. Techniques in the present disclosure can also be used in the context of these priority applications. For example, stimulation parameters, as described above, can be chosen based on the techniques described within the incorporated applications.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of providing spinal cord stimulation (SCS) therapy to a patient using a spinal cord stimulator comprising an implantable pulse generator (IPG) and a plurality of electrodes implantable in the patient and an external controller configured to be used by the patient for controlling the IPG, the method comprising:

following a fitting procedure whereby a clinician uses a clinician programmer to cause the IPG to provide supra-perception stimulation to the patient and determine an overlap of paresthesia with a location of pain the patient, enabling the IPG to provide sub-perception therapeutic stimulation to the patient, wherein the sub-perception therapeutic stimulation is configured to provide pain relief, using a graphical user interface (GUI) on a screen of the external controller to determine an indication of efficacy of the provided sub-perception therapeutic stimulation, wherein the external controller is different than the clinician programmer, based on the indication of efficacy, automatically determining via an evaluation algorithm stored in a memory of the external controller, whether to perform a reprogramming algorithm stored in a memory of the external controller to adjust one or more stimulation parameters, wherein the reprogramming algorithm:

determines whether to use sub-perception stimulation or supra-perception stimulation for reprogramming, if sub-perception stimulation is determined for reprogramming, performs a sub-perception reprogramming algorithm stored in a memory of the external controller to reprogram the IPG, and if supra-perception stimulation is determined for reprogramming, performs a supra-perception reprogramming algorithm stored in a memory of the external controller to reprogram the IPG and then automatically enables the IPG to provide sub-perception stimulation with the adjusted one or more stimulation parameters.

2. The method of claim 1, wherein the external controller is a hand-held mobile computing device.

3. The method of claim 1, wherein determining whether to perform a reprogramming algorithm comprises comparing the determined indication of efficacy to a history of prior indications of efficacy provided by the patient to determine a trend of efficacy indications.

4. The method of claim 1, wherein the indication of efficacy comprises a patient rating of the efficacy.

5. The method of claim 1, wherein determining whether to use sub-perception stimulation or supra-perception stimulation for reprogramming comprises obtaining an indication from the patient via the external controller indicating a preference for reprogramming using sub-perception stimulation or supra-perception stimulation.

6. The method of claim 1, wherein the sub-perception reprogramming algorithm comprises:

enabling the IPG to sequentially perform a plurality of stimulation programs, wherein each stimulation program comprises stimulation parameters that provide sub-perception stimulation to a different anatomical location of the patient, for each stimulation program, determining an indication of efficacy of the stimulation provided at the different anatomical location via the external controller, based on the indications of efficacy of the stimulation provided at the different anatomical locations, determining a best anatomical location for stimulation, and reprogramming the IPG to provide stimulation to the determined best anatomical location.

7. The method of claim 6, wherein the plurality of stimulation programs is pre-loaded in the IPG.

8. The method of claim 6, wherein the indications of efficacy of the stimulation provided at the different anatomical locations comprise patient ratings of the efficacy of the stimulation provided at the different anatomical locations.

9. The method of claim 6, wherein the sub-perception reprogramming algorithm further comprises adjusting the neural dose of the stimulation provided at the determined best anatomical location.

10. The method of claim 1, wherein the supra-perception reprogramming algorithm comprises:

determining whether to use pre-loaded rescue stimulation locations or patient-controlled stimulation locations for reprogramming, if using pre-loaded rescue stimulation locations for reprogramming is determined, performing a rescue location algorithm, and if using patient-controlled stimulation locations for reprogramming is determined, performing a patient-controlled location algorithm.

11. The method of claim 10, wherein the rescue location algorithm comprises:

enabling the IPG to sequentially perform a plurality of stimulation programs, wherein each stimulation program comprises stimulation parameters that provide supra-perception stimulation at different locations in the patient, for each stimulation program, determining an indication of the patient's satisfaction with the supra-perception stimulation, based on the indications of the patient's satisfaction, determining a best location for stimulation, and reprogramming the IPG to provide sub-perception stimulation to the determined best location.

12. The method of claim 11, wherein the plurality of stimulation programs is pre-loaded in the IPG.

13. The method of claim 11, wherein the indication of the patient's satisfaction with the supra-perception stimulation indicates an overlap of paresthesia evoked by the stimulation with the patient's pain.

14. The method of claim 11, wherein the supra-perception reprogramming algorithm further comprises adjusting the neural dose of the stimulation provided at the determined best location.

15. The method of claim 10, wherein the patient-controlled location algorithm comprises:

enabling the IPG to provide supra-perception stimulation at a first location, obtaining an indication from the patient indicating the patient's satisfaction with the supra-perception stimulation at the first location, enabling the IPG to move the supra-perception stimulation from a first location to a new location, obtaining an indication from the patient indicating the patient's satisfaction with the supra-perception stimulation at the new location, based on the indications of the patient's satisfaction, determining a best location for stimulation, and reprogramming the IPG to provide sub-perception stimulation to the determined best location.

16. The method of claim 15, wherein the indication of the patient's satisfaction with the supra-perception stimulation indicates an overlap of paresthesia evoked by the stimulation with the patient's pain.

17. The method of claim 15, wherein the supra-perception reprogramming algorithm further comprises adjusting the neural dose of the stimulation provided at the determined best location.

* * * * *